US009243297B2

(12) United States Patent
Vebø et al.

(10) Patent No.: US 9,243,297 B2
(45) Date of Patent: Jan. 26, 2016

(54) OLIGONUCLEOTIDE PROBE SET AND METHODS OF MICROBIOTA PROFILING

(71) Applicant: GENETIC ANALYSIS AS, Oslo (NO)

(72) Inventors: Heidi Vebø, Ás (NO); Knut Rudi, Vestby (NO); Monika Sekelja, Oslo (NO)

(73) Assignee: GENETIC ANALYSIS AS (NO)

( * ) Notice: Subject to any disclaimer, the term of this patent is extended or adjusted under 35 U.S.C. 154(b) by 0 days.

(21) Appl. No.: 13/919,056

(22) Filed: Jun. 17, 2013

(65) Prior Publication Data

US 2013/0303397 A1      Nov. 14, 2013

Related U.S. Application Data

(63) Continuation of application No. PCT/GB2011/052509, filed on Dec. 16, 2011.

(30) Foreign Application Priority Data

Dec. 16, 2010   (GB) .................................. 1021399.9

(51) Int. Cl.
*C12Q 1/68*    (2006.01)

(52) U.S. Cl.
CPC ............ *C12Q 1/689* (2013.01); *C12Q 2600/16* (2013.01)

(58) Field of Classification Search
CPC .................................................. C12Q 2600/16
USPC ............................................................ 506/9
See application file for complete search history.

(56) References Cited

U.S. PATENT DOCUMENTS

| 4,267,234 | A | 5/1981 | Rembaum |
| 4,267,235 | A | 5/1981 | Rembaum et al. |
| 4,552,812 | A | 11/1985 | Margel et al. |
| 4,677,138 | A | 6/1987 | Margel |
| 4,717,655 | A | 1/1988 | Fulwyler |
| 4,774,189 | A | 9/1988 | Schwartz |
| 5,073,498 | A | 12/1991 | Schwartz et al. |
| 5,194,300 | A | 3/1993 | Cheung |
| 5,326,692 | A | 7/1994 | Brinkley et al. |
| 5,573,909 | A | 11/1996 | Singer et al. |
| 5,716,855 | A | 2/1998 | Lerner et al. |
| 5,723,218 | A | 3/1998 | Haugland et al. |
| 5,786,219 | A | 7/1998 | Zhang et al. |

(Continued)

FOREIGN PATENT DOCUMENTS

| WO | 9714028 A2 | 4/1997 |
| WO | 9919515 A1 | 4/1999 |

(Continued)

OTHER PUBLICATIONS

Pamme et al., Anal. Chem., 2004, 76, 7250-7256.*

(Continued)

*Primary Examiner* — Larry Riggs
*Assistant Examiner* — Karla Dines
(74) *Attorney, Agent, or Firm* — Cantor Colburn LLP

(57) ABSTRACT

Described herein is a set of oligonucleotide probes. Also included are methods of using the oligonucleotide probes in profiling the microbiota of the GI tract of a subject and methods of diagnosing or monitoring a disease or condition in a subject or predicting or assessing the risk of a subject developing a disease or condition. Kits comprising the oligonucleotide probe set described herein are also provided.

6 Claims, 2 Drawing Sheets

(56) References Cited

U.S. PATENT DOCUMENTS

Figure 1:
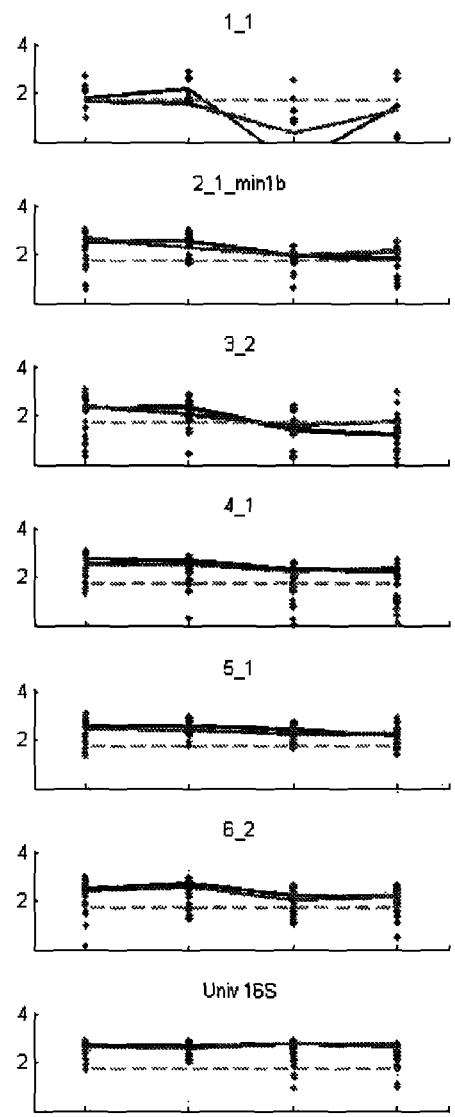

| | | | |
|---|---|---|---|
| 6,699,703 B1* | 3/2004 | Doucette-Stamm et al. | 435/252.3 |
| 7,081,341 B2* | 7/2006 | Cunningham | 435/6.13 |
| 7,919,277 B2* | 4/2011 | Russell et al. | 435/91.2 |
| 8,101,170 B2* | 1/2012 | Plail et al. | 424/93.3 |
| 8,288,137 B2* | 10/2012 | Chen et al. | 435/146 |
| 8,361,725 B2* | 1/2013 | Russell et al. | 435/6.12 |
| 2004/0126870 A1* | 7/2004 | Arigoni et al. | 435/252.2 |
| 2006/0073161 A1* | 4/2006 | Breton | 424/190.1 |
| 2008/0118923 A1 | 5/2008 | Park et al. | |
| 2009/0197249 A1 | 8/2009 | Gillevet | |
| 2009/0306230 A1 | 12/2009 | Semikhodskii et al. | |
| 2010/0279882 A1* | 11/2010 | Ronaghi et al. | 506/8 |

FOREIGN PATENT DOCUMENTS

| | | |
|---|---|---|
| WO | 0039587 A1 | 7/2000 |
| WO | 0113119 A1 | 2/2001 |
| WO | 0113120 A1 | 2/2001 |
| WO | 0118524 A2 | 3/2001 |
| WO | 0159432 A2 | 8/2001 |
| WO | 0200336 A2 | 1/2002 |
| WO | 2009123736 A2 | 10/2009 |
| WO | 2011043654 A1 | 4/2011 |

OTHER PUBLICATIONS

Rozen et al., Methods in Molecular Biology, 2000, vol. 132: Bioinfomatics Methods and Protocols, pp. 365-386.*

Nolan et al., Nature Protocols, vol. 1, No. 3, Nov. 9, 2006, pp. 1559-1582.*

Lowe et al., Nucleic Acids Research, 18(7), 1990, pp. 1757-1761.*

Rouillard et al., Nucleic Acids Research, 2003, 31(12), pp. 3057-3062.*

Cox et al.; "Lactobacillus Casei Abundance is Associated with Profound Shifts in the Infant Gut Microbiome"; PLOS One; 5(1); e8745. doi:10.1371/Journal.pone.0008745, pp. 1-8 (2010).

Eggesbo et al.; "Development of Gut Microbiota in Infants Not Exposed to Medical Interventions"; APMIS; 119(1); pp. 17-35; (2010).

Hong, et al.; "Comparative Analysis of Fecal Microbiota in Infants With and Without Eczema"; PLOS One; 5(4); e9964. doi:10.1371/Journal/plone.0009964; pp. 1-10; (2010).

Kirjavainen et al.; "Aberrant Composition of Gut Microbiota of Allergic Infants: A Target of Bifidobacterial Therapy at Weaning?"; GUT; 51(1); pp. 51-55; (2002).

Oien et al.; "Intestinal Microbiota and its Effect on the Immune System—A Nested Case-Cohort Study on Prevention of Atopy Among Small Children in Trondheim: The IMPACT study"; Contemporary Clinical Trials; 27(4); pp. 389-395; (2006).

Paliy et al.; "High-throughput Quantitative Analysis of the Human Intestinal Microbiota with a Phylogenetic Microarray"; Applied and Environmental Microbiology; 75(11); pp. 3572-3579;(2009).

Palmer, et al.; "Rapid Quantitative Profiling of Complex Microbial Populations"; Nucleic Acids Research 34(1); doi.10.1093/narj/gnj007; pp. 1-10; (2006).

Palmer et al.; "Development of the Human Infant Intestinal Microbiota"; PLOS Biology; 5(7); pp. 1556-1573; (2007).

International Search Report and Written Opinion; International Application No. PCT/GB2011/052509; International Filing Date Dec. 16, 2011; Date of Mailing Apr. 29, 2013; 21 pages.

Penders et al.; "Gut Microbiota Composition and Development of Atopic Manifestations in Infancy: the Koala Birth Cohort Study"; GUT; 56(5); pp. 661-667; (2007).

Rajilic-Stojanovic et al.; "Development and Application of the Human Intestinal Tract Chip, a Phylogenetic Microarray: Analysis of Universally Conserved Phylotypes in the Abundant Microbiota of Young and Elderly Adults"; Environmental Microbiology; 11(7); pp. 1736-1751; (2009).

van Zwol et al; "Intestinal Microbiota in Allergic and Nonallergic 1-Year-Old Very Low Birth Weight Infants After Neonatal Glutamine Supplementation"; ACTA Paediatric, International Journal of Paediatrics; 99(12); pp. 1868-1874; (2010).

Vebo et al.; "Temporal Development of the Infant Gut Microbiota in Immunoglobulin E-Sensitized and Nonsensitized Children Determined by the GA-Map Infant Array"; Clin. Vaccine Immunol; 18(8); pp. 1326-1335; (2011).

Rudi et al.; "Alignment-independent Bilinear Multivariate Modelling (AIBIMM) for Global Analyses of 16S rRNA Gene Phylogeny"; International Journal of Systematic and Evolutionary Microbiology; 56;pp. 1565-1565; (2006).

Rudi et al.; "Alignment-Independent Comparisons of Human Gastrointestinal Tract Microbial Communities in a Multidimensional 16S rRNA Gene Evolutionary Space"; Applied and Environmental Microbiology; 73(8); pp. 2727-2734; (2007).

Vebo et al.; Supplemental Material to "Temporal Development of the Infant Gut Microbiota in Immunoglobulin E-Sensitized and Nonsensitized Children Determined by GA-Map Infant array" Clinical and Vaccine Immunology; 18(8); pp. 1326-1335 (2011).

ABD-ELSAM, Kamel A.; "Bioinformatic Tools and Guideline for PCR Primer Design"; African Journal of Biotechnology; 2(5); pp. 91-95; (2003).

* cited by examiner

SEQUENCE LISTING

<160> NUMBER OF SEQ ID NOS: 56

<210> SEQ ID NO 1
<211> LENGTH: 13
<212> TYPE: DNA
<213> ORGANISM: Artificial Sequence
<220> FEATURE:
<223> OTHER INFORMATION: Probe

<400> SEQUENCE: 1
acgcttgcac cct                                                          13

<210> SEQ ID NO 2
<211> LENGTH: 22
<212> TYPE: DNA
<213> ORGANISM: Artificial Sequence
<220> FEATURE:
<223> OTHER INFORMATION: Probe

<400> SEQUENCE: 2
cgatccgaaa accttcttca ct                                                22

<210> SEQ ID NO 3
<211> LENGTH: 16
<212> TYPE: DNA
<213> ORGANISM: Artificial Sequence
<220> FEATURE:
<223> OTHER INFORMATION: Probe

<400> SEQUENCE: 3
ggacaacgct tgccac                                                       16

<210> SEQ ID NO 4
<211> LENGTH: 19
<212> TYPE: DNA
<213> ORGANISM: Artificial Sequence
<220> FEATURE:
<223> OTHER INFORMATION: Probe

<400> SEQUENCE: 4
cgtaggcggt tcgtcgcgt                                                    19

<210> SEQ ID NO 5
<211> LENGTH: 22
<212> TYPE: DNA
<213> ORGANISM: Artificial Sequence
<220> FEATURE:
<223> OTHER INFORMATION: Probe

<400> SEQUENCE: 5
ttgcggctca accgtaaaat tg                                                22

<210> SEQ ID NO 6
<211> LENGTH: 26
<212> TYPE: DNA
<213> ORGANISM: Artificial Sequence
<220> FEATURE:
<223> OTHER INFORMATION: Probe

<400> SEQUENCE: 6
gcactcaaga catccagtat caactg                                            26

<210> SEQ ID NO 7
<211> LENGTH: 19
<212> TYPE: DNA
<213> ORGANISM: Artificial Sequence

```
<220> FEATURE:
<223> OTHER INFORMATION: Probe

<400> SEQUENCE: 7
agggcagtca tccttcacg                                                    19

<210> SEQ ID NO 8
<211> LENGTH: 27
<212> TYPE: DNA
<213> ORGANISM: Artificial Sequence
<220> FEATURE:
<223> OTHER INFORMATION: Probe

<400> SEQUENCE: 8
caatcggagt tcttcgtgat atctaag                                           27

<210> SEQ ID NO 9
<211> LENGTH: 28
<212> TYPE: DNA
<213> ORGANISM: Artificial Sequence
<220> FEATURE:
<223> OTHER INFORMATION: Probe

<400> SEQUENCE: 9
tgttgtggtt ataaccgca gcaattga                                           28

<210> SEQ ID NO 10
<211> LENGTH: 15
<212> TYPE: DNA
<213> ORGANISM: Artificial Sequence
<220> FEATURE:
<223> OTHER INFORMATION: Probe

<400> SEQUENCE: 10
tccaatgacc ctccc                                                        15

<210> SEQ ID NO 11
<211> LENGTH: 16
<212> TYPE: DNA
<213> ORGANISM: Artificial Sequence
<220> FEATURE:
<223> OTHER INFORMATION: Probe

<400> SEQUENCE: 11
cactctcaca cccgtt                                                       16

<210> SEQ ID NO 12
<211> LENGTH: 17
<212> TYPE: DNA
<213> ORGANISM: Artificial Sequence
<220> FEATURE:
<223> OTHER INFORMATION: Probe

<400> SEQUENCE: 12
gttgctcggt cagactt                                                      17

<210> SEQ ID NO 13
<211> LENGTH: 20
<212> TYPE: DNA
<213> ORGANISM: Artificial Sequence
<220> FEATURE:
<223> OTHER INFORMATION: Probe

<400> SEQUENCE: 13
cgtggctttc tgattaggta                                                   20
```

```
<210> SEQ ID NO 14
<211> LENGTH: 21
<212> TYPE: DNA
<213> ORGANISM: Artificial Sequence
<220> FEATURE:
<223> OTHER INFORMATION: Probe

<400> SEQUENCE: 14
tgcttattca acgggtaaac t                                              21

<210> SEQ ID NO 15
<211> LENGTH: 21
<212> TYPE: DNA
<213> ORGANISM: Artificial Sequence
<220> FEATURE:
<223> OTHER INFORMATION: Probe

<400> SEQUENCE: 15
ccgtcactcg gctaccattt c                                              21

<210> SEQ ID NO 16
<211> LENGTH: 19
<212> TYPE: DNA
<213> ORGANISM: Artificial Sequence
<220> FEATURE:
<223> OTHER INFORMATION: Probe

<400> SEQUENCE: 16
gattttccac tcccaccat                                                 19

<210> SEQ ID NO 17
<211> LENGTH: 15
<212> TYPE: DNA
<213> ORGANISM: Artificial Sequence
<220> FEATURE:
<223> OTHER INFORMATION: Probe

<400> SEQUENCE: 17
ccgtcaaggg acaag                                                     15

<210> SEQ ID NO 18
<211> LENGTH: 24
<212> TYPE: DNA
<213> ORGANISM: Artificial Sequence
<220> FEATURE:
<223> OTHER INFORMATION: Probe

<400> SEQUENCE: 18
cggtgcttat tcgaaaggta cact                                           24

<210> SEQ ID NO 19
<211> LENGTH: 17
<212> TYPE: DNA
<213> ORGANISM: Artificial Sequence
<220> FEATURE:
<223> OTHER INFORMATION: Probe

<400> SEQUENCE: 19
cgcctgcctc aaacata                                                   17

<210> SEQ ID NO 20
<211> LENGTH: 28
<212> TYPE: DNA
<213> ORGANISM: Artificial Sequence
<220> FEATURE:
<223> OTHER INFORMATION: Probe
```

```
<400> SEQUENCE: 20
caggtgtagc ggtgaaatgc gtagagat                                          28

<210> SEQ ID NO 21
<211> LENGTH: 11
<212> TYPE: DNA
<213> ORGANISM: Artificial Sequence
<220> FEATURE:
<223> OTHER INFORMATION: Probe

<400> SEQUENCE: 21
acgctcgcac c                                                            11

<210> SEQ ID NO 22
<211> LENGTH: 18
<212> TYPE: DNA
<213> ORGANISM: Artificial Sequence
<220> FEATURE:
<223> OTHER INFORMATION: Probe

<400> SEQUENCE: 22
cggggatttc acatctga                                                     18

<210> SEQ ID NO 23
<211> LENGTH: 20
<212> TYPE: DNA
<213> ORGANISM: Artificial Sequence
<220> FEATURE:
<223> OTHER INFORMATION: Probe

<400> SEQUENCE: 23
tgccagtttc gaatgcagtt                                                   20

<210> SEQ ID NO 24
<211> LENGTH: 19
<212> TYPE: DNA
<213> ORGANISM: Artificial Sequence
<220> FEATURE:
<223> OTHER INFORMATION: Probe

<400> SEQUENCE: 24
gtgcttcttc tgcgggtaa                                                    19

<210> SEQ ID NO 25
<211> LENGTH: 18
<212> TYPE: DNA
<213> ORGANISM: Artificial Sequence
<220> FEATURE:
<223> OTHER INFORMATION: Probe

<400> SEQUENCE: 25
gctacacatg gagttcca                                                     18

<210> SEQ ID NO 26
<211> LENGTH: 15
<212> TYPE: DNA
<213> ORGANISM: Artificial Sequence
<220> FEATURE:
<223> OTHER INFORMATION: Probe

<400> SEQUENCE: 26
cgtagttagc cgtgg                                                        15

<210> SEQ ID NO 27
```

```
<211> LENGTH: 13
<212> TYPE: DNA
<213> ORGANISM: Artificial Sequence
<220> FEATURE:
<223> OTHER INFORMATION: Probe

<400> SEQUENCE: 27
agggtgcaag cgt                                                          13

<210> SEQ ID NO 28
<211> LENGTH: 22
<212> TYPE: DNA
<213> ORGANISM: Artificial Sequence
<220> FEATURE:
<223> OTHER INFORMATION: Probe

<400> SEQUENCE: 28
agtgaagaag gttttcggat cg                                                22

<210> SEQ ID NO 29
<211> LENGTH: 16
<212> TYPE: DNA
<213> ORGANISM: Artificial Sequence
<220> FEATURE:
<223> OTHER INFORMATION: Probe

<400> SEQUENCE: 29
gtggcaagcg ttgtcc                                                       16

<210> SEQ ID NO 30
<211> LENGTH: 19
<212> TYPE: DNA
<213> ORGANISM: Artificial Sequence
<220> FEATURE:
<223> OTHER INFORMATION: Probe

<400> SEQUENCE: 30
acgcgacgaa ccgcctacg                                                    19

<210> SEQ ID NO 31
<211> LENGTH: 22
<212> TYPE: DNA
<213> ORGANISM: Artificial Sequence
<220> FEATURE:
<223> OTHER INFORMATION: Probe

<400> SEQUENCE: 31
caattttacg gttgagccgc aa                                                22

<210> SEQ ID NO 32
<211> LENGTH: 26
<212> TYPE: DNA
<213> ORGANISM: Artificial Sequence
<220> FEATURE:
<223> OTHER INFORMATION: Probe

<400> SEQUENCE: 32
cagttgatac tggatgtctt gagtgc                                            26

<210> SEQ ID NO 33
<211> LENGTH: 19
<212> TYPE: DNA
<213> ORGANISM: Artificial Sequence
<220> FEATURE:
<223> OTHER INFORMATION: Probe

<400> SEQUENCE: 33
```
cgtgaaggat gactgccct                                              19

<210> SEQ ID NO 34
<211> LENGTH: 27
<212> TYPE: DNA
<213> ORGANISM: Artificial Sequence
<220> FEATURE:
<223> OTHER INFORMATION: Probe

<400> SEQUENCE: 34
cttagatatc acgaagaact ccgattg                                      27

<210> SEQ ID NO 35
<211> LENGTH: 28
<212> TYPE: DNA
<213> ORGANISM: Artificial Sequence
<220> FEATURE:
<223> OTHER INFORMATION: Probe

<400> SEQUENCE: 35
tcaattgctg cggttattaa ccacaaca                                     28

<210> SEQ ID NO 36
<211> LENGTH: 15
<212> TYPE: DNA
<213> ORGANISM: Artificial Sequence
<220> FEATURE:
<223> OTHER INFORMATION: Probe

<400> SEQUENCE: 36
gggagggtca ttgga                                                   15

<210> SEQ ID NO 37
<211> LENGTH: 16
<212> TYPE: DNA
<213> ORGANISM: Artificial Sequence
<220> FEATURE:
<223> OTHER INFORMATION: Probe

<400> SEQUENCE: 37
aacgggtgtg agagtg                                                  16

<210> SEQ ID NO 38
<211> LENGTH: 17
<212> TYPE: DNA
<213> ORGANISM: Artificial Sequence
<220> FEATURE:
<223> OTHER INFORMATION: Probe

<400> SEQUENCE: 38
aagtctgacc gagcaac                                                 17

<210> SEQ ID NO 39
<211> LENGTH: 20
<212> TYPE: DNA
<213> ORGANISM: Artificial Sequence
<220> FEATURE:
<223> OTHER INFORMATION: Probe

<400> SEQUENCE: 39
tacctaatca gaaagccacg                                              20

<210> SEQ ID NO 40
<211> LENGTH: 21
<212> TYPE: DNA

```
<213> ORGANISM: Artificial Sequence
<220> FEATURE:
<223> OTHER INFORMATION: Probe

<400> SEQUENCE: 40
agtttacccg ttgaataagc a                                              21

<210> SEQ ID NO 41
<211> LENGTH: 21
<212> TYPE: DNA
<213> ORGANISM: Artificial Sequence
<220> FEATURE:
<223> OTHER INFORMATION: Probe

<400> SEQUENCE: 41
gaaatggtag ccgagtgacg g                                              21

<210> SEQ ID NO 42
<211> LENGTH: 19
<212> TYPE: DNA
<213> ORGANISM: Artificial Sequence
<220> FEATURE:
<223> OTHER INFORMATION: Probe

<400> SEQUENCE: 42
atggtgggag tggaaaatc                                                 19

<210> SEQ ID NO 43
<211> LENGTH: 15
<212> TYPE: DNA
<213> ORGANISM: Artificial Sequence
<220> FEATURE:
<223> OTHER INFORMATION: Probe

<400> SEQUENCE: 43
cttgtcccct tgacgg                                                    15

<210> SEQ ID NO 44
<211> LENGTH: 24
<212> TYPE: DNA
<213> ORGANISM: Artificial Sequence
<220> FEATURE:
<223> OTHER INFORMATION: Probe

<400> SEQUENCE: 44
agtgtaccct ttcgaataagc accg                                          24

<210> SEQ ID NO 45
<211> LENGTH: 17
<212> TYPE: DNA
<213> ORGANISM: Artificial Sequence
<220> FEATURE:
<223> OTHER INFORMATION: Probe

<400> SEQUENCE: 45
tatgtttgag gcaggcg                                                   17

<210> SEQ ID NO 46
<211> LENGTH: 28
<212> TYPE: DNA
<213> ORGANISM: Artificial Sequence
<220> FEATURE:
<223> OTHER INFORMATION: Probe

<400> SEQUENCE: 46
atctctacgc atttcaccgc tacacctg                                       28
```

```
<210> SEQ ID NO 47
<211> LENGTH: 11
<212> TYPE: DNA
<213> ORGANISM: Artificial Sequence
<220> FEATURE:
<223> OTHER INFORMATION: Probe

<400> SEQUENCE: 47
ggtgcgagcg t                                                          11

<210> SEQ ID NO 48
<211> LENGTH: 18
<212> TYPE: DNA
<213> ORGANISM: Artificial Sequence
<220> FEATURE:
<223> OTHER INFORMATION: Probe

<400> SEQUENCE: 48
tcagatgtga aatccccg                                                   18

<210> SEQ ID NO 49
<211> LENGTH: 20
<212> TYPE: DNA
<213> ORGANISM: Artificial Sequence
<220> FEATURE:
<223> OTHER INFORMATION: Probe

<400> SEQUENCE: 49
aactgcattc gaaactggca                                                 20

<210> SEQ ID NO 50
<211> LENGTH: 19
<212> TYPE: DNA
<213> ORGANISM: Artificial Sequence
<220> FEATURE:
<223> OTHER INFORMATION: Probe

<400> SEQUENCE: 50
ttacccgcag aagaagcac                                                  19

<210> SEQ ID NO 51
<211> LENGTH: 18
<212> TYPE: DNA
<213> ORGANISM: Artificial Sequence
<220> FEATURE:
<223> OTHER INFORMATION: Probe

<400> SEQUENCE: 51
tggaactcca tgtgtagc                                                   18

<210> SEQ ID NO 52
<211> LENGTH: 15
<212> TYPE: DNA
<213> ORGANISM: Artificial Sequence
<220> FEATURE:
<223> OTHER INFORMATION: Probe

<400> SEQUENCE: 52
ccacggctaa ctacg                                                      15

<210> SEQ ID NO 53
<211> LENGTH: 18
<212> TYPE: DNA
<213> ORGANISM: Artificial Sequence
<220> FEATURE:
```

```
<223> OTHER INFORMATION: Probe

<400> SEQUENCE: 53
tcctacggga ggcagcag                                                    18

<210> SEQ ID NO 54
<211> LENGTH: 20
<212> TYPE: DNA
<213> ORGANISM: Artificial Sequence
<220> FEATURE:
<223> OTHER INFORMATION: Probe

<400> SEQUENCE: 54
cggttacctt gttacgactt                                                  20

<210> SEQ ID NO 55
<211> LENGTH: 22
<212> TYPE: DNA
<213> ORGANISM: Artificial Sequence
<220> FEATURE:
<223> OTHER INFORMATION: Probe

<400> SEQUENCE: 55
cgtattaccg cggctgctgg ca                                               22

<210> SEQ ID NO 56
<211> LENGTH: 20
<212> TYPE: DNA
<213> ORGANISM: Artificial Sequence
<220> FEATURE:
<223> OTHER INFORMATION: Probe

<400> SEQUENCE: 56
gtagcattcg attcgggcaa                                                  20
```

OLIGONUCLEOTIDE PROBE SET AND METHODS OF MICROBIOTA PROFILING

CROSS-REFERENCE TO RELATED APPLICATIONS

This is a continuation application of International Patent Application No. PCT/GB2011/052509, entitled OLIGONUCLEOTIDE PROBE SET AND METHODS OF MICROBIOTA PROFILING, filed on Dec. 16, 2011, which claims the benefit of priority to GB Application No. 1021399.9, filed on Dec. 16, 2010, by inventors: HEIDI VEBØ, KNUT RUDI, and MONIKA SEKELJA, which are incorporated herein by reference.

DETAILED DESCRIPTION

The present invention relates to a set of oligonucleotide probes and their use to profile the microbiota of the gastrointestinal (GI) tract. GI tract microbiota profiles characteristic of a disease or condition or the risk of developing a disease or condition can be identified therefore. These characteristic microbiota profiles can then be used in the diagnosis or monitoring of such diseases and conditions. The probe set may be provided in kit form.

The GI tract, also referred to as the digestive tract or alimentary canal (and which terms may be used interchangeably with GI tract) is the continuous series of organs beginning at the mouth and ending at the anus. Throughout its length the GI tract is colonised by microorganisms of a variety of different species. Together the microorganism content of the GI tract is the microbiota of the GI tract and the relative amounts of the constituent microorganisms can be considered to be a profile of the microbiota. Microbiota and microbiota profiles of different regions of the GI tract can also be determined.

Many diseases and conditions, or stages thereof, are believed to be linked to characteristic profiles of the microbiota of the GI tract, or regions thereof. In some instances the disease or condition may be caused by, or is exacerbated by, perturbations in the profile of the microbiota of the GI tract. In other instances the disease or condition causes, or by some mechanism results in, the display of a particular profile of the microbiota of the GI tract. Accordingly, by analysing microbiota profiles in GI tract samples, information can be provided that permit risk of developing a disease or condition, which has been determined to be characterised by a particular microbiota profile.

Diseases and conditions affecting the GI tract are very likely to result in characteristic microbiota profiles, e.g. Inflammatory Bowel Disease (IBD), Crohn's Disease (CD), Ulcerative Colitis (UC), Irritable Bowel Syndrome (IBS) and GI tract cancers (e.g. cancer of the mouth, pharynx, oesophagus, stomach, duodenum, jejunum, ileum, cecum, colon, rectum or anus) and evidence also exists of links between GI tract microbiota and diseases and conditions that are considered to be unrelated to the GI tract, for instance the atopic diseases, e.g. eczema, asthma, atopic dermatitis, allergic conjunctivitis, allergic rhinitis and food allergies; metabolic disorders, e.g. diabetes mellitus (type 1 and type 2), obesity and metabolic syndrome; neurological disorders, e.g. depression, multiple sclerosis, dementia, and Alzheimer's disease; and autism.

A set of probes has now been identified that can analyse with a high degree of sensitivity and accuracy the relative amounts of key constituent bacteria of the microbiota of the GI tract and thereby provide profiles of the GI tract microbiota that are sufficiently detailed and accurate to be characteristic of various diseases or conditions or the risk of developing various diseases or conditions. Consequently the newly identified probe set is a powerful diagnostic tool of high sensitivity and accuracy.

Thus, in one aspect there is provided a set of oligonucleotide probes, said set comprising:

(a) an oligonucleotide comprising a nucleotide sequence selected from ACGCTTGCACCCT (SEQ ID NO 1), the sequence complementary thereto (AGGGTGCAAGCGT; SEQ ID NO 27) or a sequence capable of hybridising to either sequence under conditions of high stringency;

(b) an oligonucleotide comprising a nucleotide sequence selected from CGATCCGAAAACCTTCTTCACT (SEQ ID NO 2), the sequence complementary thereto (AGTGAAGAAGGTTTTCGGATCG; SEQ ID NO 28) or a sequence capable of hybridising to either sequence under conditions of high stringency;

(c) an oligonucleotide comprising a nucleotide sequence selected from GGACAACGCTTGCCAC (SEQ ID NO 3), the sequence complementary thereto (GTGGCAAGCGTTGTCC; SEQ ID NO 29) or a sequence capable of hybridising to either sequence under conditions of high stringency;

(d) an oligonucleotide comprising a nucleotide sequence selected from CGTAGGCGGTTCGTCGCGT (SEQ ID NO 4), the sequence complementary thereto (ACGCGACGAACCGCCTACG; SEQ ID NO 30) or a sequence capable of hybridising to either sequence under conditions of high stringency; and (e) one or more oligonucleotides comprising a nucleotide sequence selected from those recited in Table 1 or a sequence capable of hybridising to any nucleotide sequence recited in Table 1 under conditions of high stringency; and optionally (f) one or more oligonucleotides comprising a nucleotide sequence selected from those recited in Table 2 and Table 3 or a sequence capable of hybridising to any nucleotide sequence recited in Table 2 and Table 3 under conditions of high stringency.

In preferred embodiments component (f) is present in the probe set and is one or more oligonucleotides comprising a nucleotide sequence selected from those recited in Table 2.

Any and all combinations of the various individual options for each component are specifically contemplated and hereby disclosed.

Thus, in certain other embodiments the oligonucleotide probe set comprises components (a) to (d) and optionally component (f) all as defined above and at least one of (i) an oligonucleotide comprising a nucleotide sequence selected from SEQ ID NO 5, SEQ ID NO 31 or a sequence capable of hybridising to either sequence under conditions of high stringency, (ii) an oligonucleotide comprising a nucleotide sequence selected from SEQ ID NO 6, SEQ ID NO 32 or a sequence capable of hybridising to either sequence under conditions of high stringency, (iii) an oligonucleotide comprising a nucleotide sequence selected from SEQ ID NO 7, SEQ ID NO 33 or a sequence capable of hybridising to either sequence under conditions of high stringency, (iv) an oligonucleotide comprising a nucleotide sequence selected from SEQ ID NO 8, SEQ ID NO 34 or a sequence capable of hybridising to either sequence under conditions of high stringency.

The probe set may, and typically will, comprise more than one copy of each selected oligonucleotide probe species.

Additional oligonucleotide probes may be present in the probe set. Preferably the additional oligonucleotide probes will contribute to the information on the content of GI tract microbiota that the probe set may provide. This may be by the additional probes providing positive information on the microbiota of the GI tract or by providing information that may act as a control for one or more of the other probes in the probe set or standardised information that might permit quantification of the information obtained from one or more of the other probes in the probe set. The additional probes may target the same or different bacteria as one or more of the probes of the probe set defined above.

The invention also provides an oligonucleotide probe comprising a nucleotide sequence selected from any one of SEQ ID NOs 1-52 or a nucleotide sequence capable of hybridising to said nucleotide sequence under conditions of high stringency. The use of such probes in the products of the invention and in their preparation, and the use of such probes in the methods of the invention are further aspects of the invention.

In the following, references to "the nucleotide sequence of SEQ ID NO X", also include reference to nucleotide sequences capable of hybridising under high stringency conditions to SEQ ID NO X unless the context dictates otherwise.

The oligonucleotides of the probe set of the invention may vary in size depending on which nucleotide sequence they comprise. Generally, the oligonucleotides may comprise up to 100 nucleotides, preferably up to 80, 60, 50, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 or up to 10 nucleotides. The oligonucleotides of the probe set of the invention may comprise at least 9, preferably at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 60, or at least 80 nucleotides. In certain embodiments, the oligonucleotides of the probe set of the invention may comprise at least 1, 2, 3, 4, 5, 6, 7, 8, 9, 10, 11, 12, 13, 14, 15, 16, 17, 18, 19, 20, 21, 22, 23, 24, 25, 30, 40, 60, or at least 80 nucleotides in addition to the number of nucleotides in whichever sequence of SEQ ID NOs 1 to 52 that is present in the oligonucleotide.

The nucleotides of the oligonucleotides of the probe set can be any type of nucleotide so long as hybridisation specificity or efficiency and, if necessary, nucleic acid polymerisation efficiency or primer dependent nucleic acid amplification efficiency is not detrimentally affected. The oligonucleotides may therefore be deoxyribonucleotides, ribonucleotides, modifications thereof (e.g. PNA, morpholino-, LNA) and mixtures thereof. DNA oligonucleotides and LNA modified DNA oligonucleotides are preferred.

The nucleotides corresponding to SEQ ID NOs 1 to 52 may be found in any part of the oligonucleotide probes so long as the oligonucleotides can hybridise to the complementary target sequence of the SEQ NO under consideration and, if required, can effect a nucleic acid extension reaction. In some embodiments the 3' nucleotide of whichever sequence of SEQ ID NOs 1 to 52 that is present in the oligonucleotide is the 3' nucleotide of the oligonucleotide.

In other embodiments the oligonucleotides consist essentially of a sequence selected from SEQ ID NOs 1 to 52. Thus, the oligonucleotides will have a nucleotide sequence selected from SEQ ID NOs 1 to 52 and 1, 2, 3, 4, or 5 additional nucleotides. In other embodiments the oligonucleotides will consist of a sequence selected from SEQ ID NOs 1 to 52.

Unless otherwise stated, or dictated by specific context, all nucleotide sequences are recited herein 5' to 3' in line with convention in this technical field.

High stringency conditions for hybridisation are defined as 2×SSC/50% formamide at 50° C. for binding conditions and 2×SSC at 65° C. for washing conditions (where SSC=0.15 M NaCl, 0.015 M sodium citrate, pH 7.2).

In preferred embodiments the nucleotide sequences that can hybridise to one of SEQ ID NOs. 1 to 52 under high stringency conditions will hybridise to all, or substantially all, of the nucleotides in the sequences of SEQ ID NOs 1 to 52, e.g. a series of contiguous nucleotides with a number of nucleotides that amounts to at least 50% preferably at least 55, 60, 65, 70, 75, 80, 85, 90 or 95% of the total number of nucleotides in the sequence of the SEQ ID NO under consideration.

Viewed alternatively, nucleotide sequences that can hybridise to the nucleotide sequences of one of SEQ ID NOs. 1 to 26 or 27 to 52 under high stringency conditions may be those nucleotide sequences that correspond to the nucleotide sequence of SEQ ID NOs. 27 to 52 or 1 to 26, respectively but with up to 40% of the bases (adenine, thymine/uracil, guanine, or cytosine) in the nucleotide sequences of SEQ ID NOs. 27 to 52 or 1 to 26, being substituted with a different base. Preferably up to 35, 30, 25, 20, 15, 10 or 5% of the bases will be substituted. Put another way, nucleotide sequences that can hybridise to the nucleotide sequences of one of SEQ ID NOs. 1 to 26 or 27 to 52 under high stringency conditions may be those nucleotide sequences that correspond to the nucleotide sequence of SEQ ID NOs. 27 to 52 or 1 to 26, respectively but with up to 5, 4, 3 or 2 substituted bases or only a single base substitution. The base being substituted into the sequence can be any standard or non-standard, naturally occurring or synthetic base.

Nucleotide sequences that can hybridise to SEQ ID NOs. 1 to 26 or 27 to 52 under high stringency conditions will preferably be 9, 10, 11, 12, 13, 14, 15, 16, 17, 18, 19, 20, 21, 22, 23, 24, 25, 26, 27 or 28 nucleotides in length, and consist of a contiguous part of the nucleotide sequence of SEQ ID 27 to 52 or 1 to 26, respectively, with the above described substitutions.

Preferably the base substitution(s) occur at or near the 5' end of the nucleotide sequence, e.g. in the final 15, 10 or 5 5' nucleotides in the sequence. Put differently, the base substitution(s) preferably do not occur at or near the 3' end of the nucleotide sequence, e.g. in the final 2, 3, 4, 5, 10 or 15 3' nucleotides. In other embodiments the 3' nucleotide will not have a substituted base.

In certain embodiments any of the oligonucleotides of the probe set comprising a nucleotide sequence of any one of SEQ ID NOs 1 to 26 may have a C residue immediately 3' of said nucleotide sequence or any of the oligonucleotides comprising a nucleotide sequence of any of one of SEQ ID NOs 27 to 52 may have a G residue immediately 5' of said nucleotide sequence.

The oligonucleotides of the probe set may be labelled with a moiety to assist with detection or manipulation. A large number of suitable moieties and labelling methods are known in the art and described in the literature. Many moieties can perform both functions. Any detectable or signal-generating molecule or reporter molecule may be used. Convenient labels include colorimetric, chemiluminescent, chromogenic, radioactive and fluorescent labels, but enzymatic (e.g. colorimetric, luminescent, chromogenic) or antibody-based labelling methods or signal-generating systems may also be used. Thus the term "label" as used herein includes not only directly detectable signal-giving or passive moieties, but also any moiety which generates a signal or takes part in a signal generating reaction or that may be detected indirectly in some way. For instance the moiety may be biotin and detection may be indirect via streptavidin carrying a colorimetric, chemiluminescent, chromogenic, radioactive or fluorescent moiety.

The label can, in some embodiments, comprise a plurality of moieties that contributes to the overall detectable output of the label. By varying the identity and/or the relative proportions of these moieties, a wide palette of unique labels can be constructed. For instance, a plurality of dyes, e.g. luminescent (e.g. bioluminescent, chemiluminescent, photoluminescent, radioluminescent, sonoluminescent, etc.) which combine to give a unique electromagnetic spectral signature upon excitation may be used. By varying the proportions of the selected dyes further differentiation in the spectral signature can be achieved. Signatures based on the absorption of certain wavelengths of electromagnetic radiation are also envisaged.

Fluorescein or other fluorescently labelled nucleotides are particularly suitable for incorporation into the primers, and allow detection directly by fluorescence or indirectly by antibody interactions. These are commercially available. Primers can be labelled by e.g. [$^{35}$S], [$^{3}$H] or [$^{32}$P] as described in Syvänen, A. C. et al. Genomics 8, [1990], 684-692. Any binding moiety may be used as a label, for instance an antibody fragment, His-tag, biotin or streptavidin. These may be incorporated in the form of labelled nucleotides.

Some or all of the oligonucleotides of the probe set may be provided immobilised on one or more solid supports for use in the invention. In other embodiments the oligonucleotides of the probe set may be immobilised on one or more solid supports prior to use. Single or preferably multiple copies of the oligonucleotide probes are attached to said solid supports, e.g. 10 or more, e.g. at least 100 copies of each unique probe are present.

One or more oligonucleotide probes of the probe set, each of a certain sequence, may be associated with separate solid supports which together form a set of probes immobilised on multiple solid supports, e.g. one or more oligonucleotide probes of the probe set may be immobilized on multiple beads, membranes, filters, biochips etc. The solid supports of the different parts of the probe set are conveniently physically associated although the signals associated with each probe (generated as described hereinafter) must be separately determinable.

Alternatively, the probes may be immobilised on discrete portions of the same solid support, e.g. each oligonucleotide probe of a certain sequence, typically in multiple copies, may be immobilised to a distinct and discrete portion or region of a single chip, plate, filter or membrane, e.g. to generate an array.

A combination of such techniques may also be used, e.g. several solid supports may be used which each carry several probes of differing sequence immobilised thereon.

The expression "solid support" shall mean any solid material able to bind oligonucleotides, e.g. by hydrophobic, ionic or covalent interaction.

"Immobilisation" as used herein refers to reversible or irreversible association of the probes to said solid support. If reversible, the probes remain associated with the solid support for a time sufficient for methods of the invention to be carried out.

Suitable immobilising supports to which the oligonucleotides can be attached are known in the art and include any of the well known supports or matrices which are currently widely used or proposed for immobilisation, separation etc. of oligonucleotides. Such materials include, but are not limited to, any synthetic organic polymer such as polystyrene, polyvinylchloride, polyethylene; or nitrocellulose and cellulose acetate; or agarose, cellulose, alginate, teflon or latex; or tosyl activated surfaces; or glass or nylon or any surface carrying a group suited for covalent coupling of nucleic acids. These may take the form of particles, sheets, gels, filters, membranes, fibres, capillaries, chips or microtitre strips, slides, tubes, plates or wells etc. Methods of immobilising or attaching oligonucleotides to solid supports are likewise known in the art. Particularly preferred are DNA chips (microchips, glass chips) now common in molecular biology procedures. In other embodiments membrane strips on to which the oligonucleotides may be spotted and then UV cross-linked may be used. Alternatively, attachment may be performed indirectly by the use of an attachment moiety carried on the oligonucleotide probes and/or solid support. Thus for example, a pair of affinity binding partners may be used, such as avidin, streptavidin or biotin, DNA or DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the solid support and the other partner is attached to (or is inherently part of) the nucleic acid molecules.

As used herein an "affinity binding pair" refers to two components which recognize and bind to one another specifically (i.e. in preference to binding to other molecules).

Attachment of appropriate functional groups to the solid support may be performed by methods well known in the art, which include for example, attachment through hydroxyl, carboxyl, aldehyde or amino groups which may be provided by treating the solid support to provide suitable surface coatings. Solid supports presenting appropriate moieties for attachment of the binding partner may be produced by routine methods known in the art.

Attachment of appropriate functional groups to the oligonucleotide probes of the invention may be performed by ligation or introduced during synthesis or amplification, for example using primers carrying an appropriate moiety, such as biotin or a particular sequence for capture.

In certain embodiments, each oligonucleotide probe of a certain sequence may be associated with a separate solid support, e.g. a bead or a microsphere, having a particular label such that a population, or plurality of populations, of particles having the same label and the same probe immobilised thereon is formed. Detection of a hybridisation event occurring on a particle with a particular label will provide information on the sequence of the probe involved in that event.

The particles may be labelled in any convenient way, e.g. using one or more of the labels described above. In one embodiment the particle label will not be or comprise an oligonucleotide, or a nucleic acid, or a labelled oligonucleotide or labelled nucleic acid. Conveniently the particulate solid support of these embodiments will be labelled with a dye, e.g. a luminescent (e.g. bioluminescent, chemiluminescent, photoluminescent, radioluminescent, sonoluminescent, etc.) dye, or a plurality of dyes (or proportions thereof) which combine to give a unique electromagnetic spectral signature upon excitation. Signatures based on the absorption of certain wavelengths of electromagnetic radiation are also envisaged.

Conveniently the dye will be fluorescent, e.g. comprise red or infrared fluorophores, e.g. phycoerythrin.

The label may be immobilised on and/or in the particle, e.g. by direct covalent binding to the substrate of the particle or it may be bound to another molecule which is in turn immobilised on and/or in the particle. The label may also be incorporated into and/or onto the particle by non-covalent means, e.g. by entrapment, absorption or adsorption of the molecules making up the label in or on the substrate of the particle, or by entrapment in void(s) within the substrate and/or on its surface.

In other embodiments the particle comprises nanoparticles on which and/or in which the label has been immobilised or incorporated.

The label can be applied to the particle after it is produced, or the label may be incorporated or immobilised into and/or onto the particle during its production, e.g. during the cross-linking of a polymeric substrate.

Preferably the label of the probe(s) will be distinguishable from the label of the particle(s). In preferred embodiments the label of the particles will be detectable at the same time as the label of the probe(s). Preferably the labelled particles will also be magnetic, e.g. paramagnetic or superparamagnetic.

Suitable particulate solid supports are manufactured by Luminex Corp. See for instance WO01/13120, WO01/13119, WO97/14028 and WO99/19515, the contents of which are incorporated herein by reference. Further particles which may be used in the working on the invention are provided in U.S. Pat. No. 4,267,234, U.S. Pat. No. 4,267,235, U.S. Pat. No. 4,552,812, U.S. Pat. No. 4,677,138, U.S. Pat. No. 5,194,300, U.S. Pat. No. 4,774,189, U.S. Pat. No. 5,073,498, U.S. Pat. No. 4,717,655, U.S. Pat. No. 5,723,218, U.S. Pat. No. 5,326,692, U.S. Pat. No. 5,716,855, U.S. Pat. No. 5,573,909 and U.S. Pat. No. 5,786,219, the contents of which are incorporated herein by reference. Other suitable solid supports are manufactured by Illumina, Inc. See for instance WO00/39587, WO 01/18524, WO01/59432 and WO02/00336 the contents of which are incorporated herein by reference.

Preferably the support is magnetic (preferably paramagnetic or superparamagnetic) e.g. magnetic particles, for instance magnetic beads.

In other embodiments none of the oligonucleotides are used in immobilised form, and in general this is preferred.

In a preferred embodiment the oligonucleotide probe set defined herein comprises:

(a) an oligonucleotide comprising a nucleotide sequence selected from SEQ ID NO 1 or a sequence capable of hybridising to SEQ ID NO 27 under conditions of high stringency;

(b) an oligonucleotide comprising a nucleotide sequence selected from SEQ ID NO 2 or a sequence capable of hybridising to SEQ ID NO 28 under conditions of high stringency;

(c) an oligonucleotide comprising a nucleotide sequence selected from SEQ ID NO 3 or a sequence capable of hybridising to SEQ ID NO 29 under conditions of high stringency;

(d) an oligonucleotide comprising a nucleotide sequence selected from SEQ ID NO 4 or a sequence capable of hybridising to SEQ ID NO 30 under conditions of high stringency; and (e) one or more oligonucleotides comprising a nucleotide sequence selected from SEQ ID NOs 5 to 8 or a sequence capable of hybridising to SEQ ID NOs 31 to 34 under conditions of high stringency; and optionally (f) one or more oligonucleotides comprising a nucleotide sequence selected from SEQ ID NOs 9 to 18, a sequence capable of hybridising to SEQ ID NOs 35 to 44 under conditions of high stringency, a nucleotide sequence selected from SEQ ID NOs 19 to 26 or a sequence capable of hybridising to SEQ ID NOs 45 to 52 under conditions of high stringency. Preferably, in this embodiment, none of the oligonucleotide probes are immobilised on a solid support.

In other preferred embodiments the oligonucleotide probe set defined herein comprises:

(a) an oligonucleotide comprising a nucleotide sequence selected from SEQ ID NO 27 or a sequence capable of hybridising to SEQ ID NO 1 under conditions of high stringency;

(b) an oligonucleotide comprising a nucleotide sequence selected from SEQ ID NO 28 or a sequence capable of hybridising to SEQ ID NO 2 under conditions of high stringency;

(c) an oligonucleotide comprising a nucleotide sequence selected from SEQ ID NO 29 or a sequence capable of hybridising to SEQ ID NO 3 under conditions of high stringency;

(d) an oligonucleotide comprising a nucleotide sequence selected from SEQ ID NO 30 or a sequence capable of hybridising to SEQ ID NO 4 under conditions of high stringency, and (e) one or more oligonucleotides comprising a nucleotide sequence selected from SEQ ID NOs 31 to 34 or a sequence capable of hybridising to SEQ ID NOs 5 to 8 under conditions of high stringency; and optionally (f) one or more oligonucleotides comprising a nucleotide sequence selected from SEQ ID NOs 35 to 44, a sequence capable of hybridising to SEQ ID NOs 9 to 18 under conditions of high stringency, SEQ ID NOs 45 to 52 or a sequence capable of hybridising to SEQ ID NOs 19 to 26 under conditions of high stringency. Preferably, in this embodiment, all of the oligonucleotide probes are immobilised on a solid support, or a plurality of solid supports.

In a still further preferred embodiment, the oligonucleotide probe set of the invention is a combination of the preceding two preferred embodiments, in particular wherein the former preferred set of probes is not immobilised on a solid support. In other words, a kit is provided which comprises, in two discrete parts, the two preferred probe sets defined above.

The oligonucleotide probes of the probe set of the invention are capable of hybridising to sequences in bacterial 16S rRNA and rDNA that are specific for particular bacteria or groups of bacteria. SEQ ID NOs 1 and 27 are designed to target sequences in the 16S rRNA and rDNA of Proteobacteria. SEQ ID NOs 2 and 28 are designed to target sequences in the 16S rRNA and rDNA of Firmicutes (Lactobacillales, Clostridium perfringens, *Staphylococcus*). SEQ ID NOs 3 and 29 are designed to target sequences in the 16S rRNA and rDNA of Firmicutes (Clostridia, Bacillales, Enterococcus, Lactobacillus). SEQ ID NOs 4 and 30 are designed to target sequences in the 16S rRNA and rDNA of Actinobacteria. The organisms displaying the target sequences of SEQ ID NOs 5 to 26 and 31 to 52 are recited in Tables 1, 2 and 3. These bacteria are bacteria found typically in the GI tract.

The oligonucleotide probe set of the invention can therefore be used to analyse samples from the GI tract and provide a profile of the microbiota of the GI tract.

Thus in another aspect the invention provides a method of profiling the microbiota of the GI tract of a subject, said method comprising:

(i) contacting a sample from the GI tract of said subject with an oligonucleotide probe set as defined above;

(ii) subjecting the sample and the probe set to conditions which allow hybridisation of the probes to their target nucleotide sequences within nucleic acid molecules in said sample; and (iii) for each oligonucleotide in said probe set, determining the amount of its target nucleotide sequence that is present in said sample.

The profile of the microbiota of the GI tract of the subject may then be prepared from the relative amounts of said target sequence.

In this aspect of the invention the target nucleotide sequences for SEQ ID NOs 1 to 26 are the sequences fully complementary thereto, i.e. SEQ ID NOs 27 to 52, respectively. Likewise, the target nucleotide sequences for SEQ ID NOs 27 to 52 are the sequences fully complementary thereto, i.e. SEQ ID NOs 1 to 26, respectively. In certain embodiments the target nucleotide sequences for SEQ ID NOs 1 to 26 are the sequences of SEQ ID NOs 27 to 52, respectively, with a G residue immediately 5' of said nucleotide sequence. Likewise, the target nucleotide sequences for SEQ ID NOs 27 to 52 are the sequences of SEQ ID NOs 1 to 26, respectively with a C residue immediately 3' of said nucleotide sequence.

The amount of target sequence can be determined by any convenient means and many such means will be familiar to the skilled man. This can be a partially, semi- or fully quantitative measurement, but can also be a qualitative (or relative) measure in which results for each target are simply compared to one another without numerical values being affixed. As discussed later, in some embodiments quantitative measurement is performed and the data obtained is analysed with statistical techniques in order to determine the statistically significant features of the microbiota profile.

In one embodiment the amount of each target sequence is determined by using the oligonucleotides of the probe set of the invention with labels attached thereto that will allow detection by direct means or indirect means. In other words the oligonucleotide probes of the invention are used simply as conventional oligonucleotide probes. Suitable labels are described above. After contact of such probes with the sample, under conditions which allow for hybridisation of the probes to their target sequences, and typically following a step (or steps) to remove unbound labelled oligonucleotides and/or non-specifically bound oligonucleotides, the strength of the signal from the label of each probe emanating from the sample under investigation (i.e. the amount of label bound to the sample) will be proportional to the amount of hybridised oligonucleotide, and therefore its target sequence. In preferred embodiments the label is selected such that it is detectable only when the probe is hybridised to its target. In such embodiments, the need to remove the unbound probe is lessened.

Any convenient means may be used to remove any unbound or non-specifically probes, for instance with one or more washing steps (e.g. with water or a buffered solution which may contain formamide and/or a detergent), electrophoresis, centrifugation, capture onto solid supports, chromatography or any combination thereof. Suitable solid supports are described above. In another embodiment the probes may carry a binding moiety, or the label may be a binding moiety, that will allow manipulation of the probes and any part of the sample hybridised thereto. Suitable binding moieties are discussed above.

Thus, the invention provides a method of profiling the microbiota of the GI tract of a subject, said method comprising:

(i) contacting a sample from the GI tract of said subject with an oligonucleotide probe set as defined above, wherein each oligonucleotide has a label attached thereto;

(ii) subjecting the sample and the probe set to conditions which allow hybridisation of the probes to their target nucleotide sequences within nucleic acid molecules in said sample; and (iii) for each labelled oligonucleotide in said probe set, determining the amount of said label bound to said sample by determining the strength of the signal from the label emanating from the sample. The amount of label bound to the sample is indicative of the amount of the target sequence for that labelled oligonucleotide in said sample.

In a preferred embodiment the method will comprise a step between steps (i) and (ii) in which unbound oligonucleotide and/or non-specifically bound oligonucleotide is removed.

In another embodiment the amount of each target nucleotide sequence present in the sample is determined by using an oligonucleotide probe set of the invention, in particular those sets comprising oligonucleotide probes which comprise nucleotide sequences selected from SEQ ID NOs 1 to 26, as a set of probes which are labelled only when hybridised to their target sequences. In some embodiments the oligonucleotides of the probe set may already carry a label that is different to the label used to selectively label the probes. The strength of the signal from the selectively labelled probes emanating from the sample under investigation (i.e. the amount of labels bound to the sample) will be proportional to the amount of hybridised oligonucleotide and in turn the amount of target sequence.

As mentioned previously, depending on the conditions employed, this can be a partially, semi- or fully quantitative measurement, but can also be a qualitative (or relative) measure in which results for each target sequence are simply compared to one another without numerical values being affixed.

Conveniently, selective labelling may be achieved using labelled nucleotides, i.e. by incorporation into the oligonucleotide probe of a nucleotide carrying a label. In other words, selective labelling may occur by chain extension of the oligonucleotide probe using a polymerase enzyme which incorporates a labelled nucleotide, preferably a labelled dideoxynucleotide (e.g. ddATP, ddCTP, ddGTP, ddTTP, ddUTP) more preferably labelled ddCTP, most preferably a fluorescently labelled, e.g. TAMRA labelled, ddCTP or a biotin labelled ddCTP. This approach to the detection of specific nucleotide sequences is sometimes referred to as primer extension analysis. Suitable primer extension analysis techniques are well known to the skilled man, e.g. those techniques disclosed in WO99/50448, the contents of which are incorporated herein by reference. Suitable labels are described above. Fluorescent labels and biotin are mentioned in particular.

In the case of oligonucleotide probes terminating with SEQ ID NOs. 1 to 26 at their 3', the label will preferably be a labelled ddCTP, e.g a TAMRA or biotin labelled ddCTP. Most preferably in this embodiment the probe set of the invention will comprise oligonucleotides consisting of SEQ ID NOs 1 to 26 and the label will be a labelled ddCTP, e.g. a TAMRA or biotin labelled ddCTP.

Detection of the labelled probes can be by any means convenient for the label being used. The skilled man would be able to devise suitable methods based on his selection of labels. In preferred embodiments, the labels are fluorescent labels (e.g. TAMRA) and in such embodiments the fluorescently labelled probes can be detected and, if required, quantified using a device that can measure the intensity (or strength) of fluorescent signals. A biotin label may be detected indirectly by exposing the label to streptavidin, or another biotin-binding molecule, which carries a detectable moiety, e.g. a colorimetric, chemiluminescent, chromogenic, radioactive or fluorescent label. In some embodiments, detection will occur after the labelled probes have undergone manipulation to remove, at least partially, contaminants (e.g. unlabelled probes, excess label, and other reagents used in the labelling reaction). Again, the skilled man would be very familiar with techniques which can achieve this, by way of example mention is made of electrophoresis (e.g. gel, e.g. capillary gel electrophoresis), centrifugation, chromatography and filtration based techniques, capture onto solid supports, or any combination thereof.

In other preferred embodiments the selectively labelled oligonucleotide probes are detected after a step in which the oligonucleotide probes from the selective labelling step (i.e. labelled and unlabelled), or the selectively labelled oligonucleotide probes only, are hybridised to nucleotide sequences that are partially, or preferably fully, complementary to the oligonucleotide probes.

Conveniently, the complementary nucleotide sequences can be provided on one of more solid supports, e.g. those described previously.

In particularly preferred embodiments the oligonucleotide probe set which undergoes selective labelling comprises:

(a) an oligonucleotide comprising a nucleotide sequence selected from SEQ ID NO 1 or a sequence capable of hybridising to SEQ ID NO 27 under conditions of high stringency;

(b) an oligonucleotide comprising a nucleotide sequence selected from SEQ ID NO 2 or a sequence capable of hybridising to SEQ ID NO 28 under conditions of high stringency;

(c) an oligonucleotide comprising a nucleotide sequence selected from SEQ ID NO 3 or a sequence capable of hybridising to SEQ ID NO 29 under conditions of high stringency;

(d) an oligonucleotide comprising a nucleotide sequence selected from SEQ ID NO 4 or a sequence capable of hybridising to SEQ ID NO 30 under conditions of high stringency; and (e) one or more oligonucleotides comprising a nucleotide sequence selected from SEQ ID NOs 5 to 8 or a sequence capable of hybridising to SEQ ID NOs 31 to 34 under conditions of high stringency; and optionally (f) one or more oligonucleotides comprising a nucleotide sequence selected from SEQ ID NOs 9 to 18, a sequence capable of hybridising to SEQ ID NOs 35 to 44 under conditions of high stringency, SEQ ID NOs 19 to 26 or a sequence capable of hybridising to SEQ ID NOs 45 to 52 under conditions of high stringency.

Following selective labelling of the above probe set, the selectively labelled probes are applied to a solid support-bound probe set comprising:

(a) an oligonucleotide comprising a nucleotide sequence selected from SEQ ID NO 27 or a sequence capable of hybridising to SEQ ID NO 1 under conditions of high stringency;

(b) an oligonucleotide comprising a nucleotide sequence selected from SEQ ID NO 28 or a sequence capable of hybridising to SEQ ID NO 2 under conditions of high stringency;

(c) an oligonucleotide comprising a nucleotide sequence selected from SEQ ID NO 29 or a sequence capable of hybridising to SEQ ID NO 3 under conditions of high stringency;

(d) an oligonucleotide comprising a nucleotide sequence selected from SEQ ID NO 30 or a sequence capable of hybridising to SEQ ID NO 4 under conditions of high stringency; and (e) one or more oligonucleotides comprising a nucleotide sequence selected from SEQ ID NOs 31 to 34 or a sequence capable of hybridising to SEQ ID NOs 5 to 8 under conditions of high stringency; and optionally (f) one or more oligonucleotides comprising a nucleotide sequence selected from SEQ ID NOs 35 to 44, a sequence capable of hybridising to SEQ ID NOs 9 to 18 under conditions of high stringency, SEQ ID NOs 45 to 52 or a sequence capable of hybridising to SEQ ID NOs 19 to 26 under conditions of high stringency. Preferably, in this embodiment, all of the oligonucleotide probes are immobilised on one or more solid supports.

Preferably, components (e) and (f) of each probe set are selected to correspond to one another (i.e. each probe in components (e) and (f) of each probe set has a complementary sequence in components (e) and (f) of the other probe set).

The invention therefore provides a method of profiling the microbiota of the GI tract of a subject, said method comprising:

(i) contacting a sample from the GI tract of said subject with an oligonucleotide probe set as defined above, (ii) subjecting the sample and the probe set to conditions which allow hybridisation of the probes to their target nucleotide sequences within nucleic acid molecules in said sample;

(iii) selectively labelling the oligonucleotide probes of the probe set when hybridised to their target nucleotide sequence; and (iv) determining the amount of each labelled oligonucleotide probe produced in step (iii).

The amount of each labelled oligonucleotide probe is indicative of the amount of the target sequence for that labelled oligonucleotide in said sample In some embodiments, step (iv) comprises hybridisation of the oligonucleotide probes from the labelling step to nucleotide sequences complementary to those oligonucleotides.

In a further embodiment the amount of each target nucleotide sequence present in the sample is determined by labelling the nucleic acids in the sample prior to the step of contacting the sample with the oligonucleotide probe set of the invention. Simply by assessing the amount of labelled nucleic acid hybridising to the probes of the probe set the amount of the target nucleotide sequence for each oligonucleotide probe that is present in said sample can be determined. In these embodiments bacterial 16S rRNA or 16S rDNA, particularly those regions containing the target sequences for the oligonucleotides of the probe set, or nucleic acids comprising said sequences are labelled prior to contact with the probe set. Suitable labels are discussed above. Conveniently labelling occurs when the nucleic acids in the sample are amplified and/or reverse transcribed prior to contact with the probe set as discussed in more detail below. Conveniently the nucleic acids are labelled by the incorporation of labelled nucleotides during a nucleic acid amplification reaction and/or a reverse transcription reaction.

In further embodiments both the oligonucleotides of the probe set and the nucleic acids in the sample as described above are labelled with moieties that provide a signal only when in close proximity, e.g. when the probes are hybridised to their target sequences in the nucleic acid.

In another embodiment the amount of each target nucleotide sequence present in the sample is determined by using the oligonucleotides of the probe set of the invention as primers in one or more nucleic acid amplification reactions, e.g. a multiplex amplification reaction. If the appropriate conditions are selected, such a reaction can be performed such that the amount of amplification product obtained for each oligonucleotide of the probe set will be proportional to the amount of each target nucleotide sequence present in the sample. Thus, the amount of product the amplification reaction provides for each oligonucleotide of the probe set is a measure of the amount of that oligonucleotide that hybridises to the sample from the subject under investigation and is in turn proportional to the amount of target sequence for that oligonucleotide in the sample and so is proportional to the amount of bacteria that that oligonucleotide is designed to target in the sample. Accordingly, the amount of amplification product can be used to determine the levels of these bacteria in the GI tract of a subject.

As mentioned previously, depending on the conditions employed, this can be a partially, semi- or fully quantitative measurement, but can also be a qualitative (or relative) measure in which results for each target sequence are simply compared to one another without numerical values being affixed.

Amplification can be achieved by any convenient primer-dependent nucleic acid amplification reaction. Most conveniently the polymerase chain reaction (PCR) will be used, although the skilled man would be aware of other techniques. For instance LAR/LCR, SDA, Loop-mediated isothermal amplification and nucleic acid sequence based amplification (NASBA)/3SR (Self-Sustaining Sequence Replication) may be used.

Many variations of PCR have been developed, for instance Real Time PCR (also known as quantitative PCR, qPCR), hot-start PCR, competitive PCR, and so on, and these may all be employed where appropriate to the needs of the skilled man.

In one basic embodiment of the invention using a PCR based amplification the oligonucleotides of the probe set of the invention is contacted with a reaction mixture containing the sample, a suitable set of second primers to form a set of working primer pairs and free nucleotides in a suitable buffer under conditions which allow hybridisation. Thermal cycling of the resulting mixture in the presence of a DNA polymerase results in amplification of the target sequences for each oligonucleotide, i.e. sequences characteristic of the bacteria the oligonucleotides of the probe set of the invention are designed to target.

Optimal performance of the PCR process is influenced by choice of temperature, time at temperature, and length of time between temperatures for each step in the cycle. A typical cycling profile for PCR amplification is (a) 15 minutes of DNA melting at 95° C.; (b) 30 seconds of primer annealing at 50-65° C.; (c) 90 seconds of primer extending at 68-72° C.; (d) 30 seconds of DNA melting at 95° C.; and steps (b)-(d) are repeated as many times as necessary to obtain the desired level of amplification.

Modifications of the basic PCR method such as qPCR (Real Time PCR) have been developed that can provide quantitative information on the template being amplified. Numerous approaches have been taken although the two most common techniques use double-stranded DNA binding fluorescent dyes or selective fluorescent reporter probes.

Double-stranded DNA binding fluorescent dyes, for instance SYBR Green, associate with the amplification product as it is produced and when associated the dye fluoresces. Accordingly, by measuring fluorescence after every PCR cycle, the relative amount of amplification product can be monitored in real time. Through the use of internal standards and controls, this information can be translated into quantitative data on the amount of template at the start of the reaction.

The fluorescent reporter probes used in qPCR are sequence specific oligonucleotides, typically RNA or DNA, that have a fluorescent reporter molecule at one end and a quencher molecule at the other (e.g. the reporter molecule is at the 5' end and a quencher molecule at the 3' end or vice versa). The probe is designed so that the reporter is quenched by the quencher. The probe is also designed to hybridise selectively to particular regions of complementary sequence which might be in the template. If these regions are between the annealed PCR primers the polymerase, if it has exonuclease activity, will degrade (depolymerise) the bound probe as it extends the nascent nucleic acid chain it is polymerising. This will relieve the quenching and fluorescence will rise. Accordingly, by measuring fluorescence after every PCR cycle, the relative amount of amplification product can be monitored in real time. Through the use of internal standard and controls, this information can be translated into quantitative data.

Thus, in another aspect the invention provides a method of profiling the microbiota of the GI tract of a subject, said method comprising:
(i) contacting a sample from the GI tract of said subject with an oligonucleotide probe set as defined above;
(ii) subjecting the sample and the probe set to conditions which allow hybridisation of the probes to their target nucleotide sequences within nucleic acid molecules in said sample;
(iii) performing a primer-dependent nucleic acid amplification reaction; and
(iv) for each oligonucleotide in the probe set determining the amount of amplification product produced therefrom in said primer-dependent nucleic acid amplification reaction.

The amount of said product for each oligonucleotide is indicative of the amount of the target sequence for each oligonucleotide in the sample.

In a preferred embodiment step (i) will also comprise contacting the sample with a set of oligonucleotides that are capable of functioning with the oligonucleotide set of the invention in a nucleic acid amplification reaction, e.g. PCR, to produce an amplification product for each oligonucleotide of the probe set, assuming a suitable template is present in the sample. In this embodiment, when paired with a second set of suitable amplification primers, the oligonucleotides comprising SEQ ID NOs 1 to 26 will act as forward primers and oligonucleotides comprising SEQ ID NOs 27 to 52 will act as reverse primers.

In this embodiment the method may involve a plurality of primer dependent nucleic acid amplifications being run in parallel, with each reaction involving a single probe, or one or more multiplex primer dependent nucleic acid amplifications being run with two or more probes being used in the same reaction.

The amplification product from each oligonucleotide may be detected, and amounts of amplification product can be determined, by any convenient means. To some extent feasible techniques will be dictated by the number of oligonucleotides of the probe set that are used in each amplification reaction (e.g. whether the reaction is a multiplex reaction or not or the extent of multiplexing). The skilled man would be able to select appropriate techniques.

A vast number of techniques are routinely employed as standard laboratory techniques and the literature has descriptions of more specialised approaches. At its most simple the amount of amplification product may be detected or determined by visual inspection of the reaction mixture at the end of the reaction or at a desired timepoint. Typically the amplification product will be resolved with the aid of a label that may be preferentially bound to the amplification product. Typically a dye substance, e.g. a colorimetric, chromomeric fluorescent or luminescent dye (for instance ethidium bromide or SYBR green) is used. In other embodiments a labelled oligonucleotide probe that preferentially binds the amplification product, in particular a probe that binds preferentially to substantially all of the individual amplified nucleic acids in the amplification product, is used. A suitable probe might be based on the nucleotide sequence of one or more of SEQ ID NOs 1 to 52. Suitable labels for the probe are discussed above. In some embodiments the probe may be provided in an unlabelled form with labelling occurring after preferential binding to the amplification product, or preferential binding to substantially all of the individual amplified nucleic acids in the amplification product.

However, in some cases a nucleic acid precipitant (e.g. salt and/or alcohol) can simply be used to cause the amplification product to come out of solution and be visible without labelling.

To aid visualisation the components of amplification product can be dispersed in or on a solid support, for instance by electrophoresis (e.g. using agarose or polyacrylamide gels), chromatography (e.g. HPLC, TLC, affinity, gel filtration) or filtration, or a combination thereof, prior to or after contact with the label.

Depending on the label used detection can be made more accurate by using widely available detection technologies, e.g. radiation sensitive films and digital imaging technologies in combination with computer assisted image analysis, photometers, fluorometers, colorimeters, scintillation counters, and the like Preferably the amplification product is separated from the remainder of the amplification reaction before being contacted by the label, e.g. in the form of a labelled oligonucleotide probe. This may be by any convenient means, for instance with one or more washing steps (e.g. with water or a buffered solution which may contain formamide and/or a detergent), electrophoresis, centrifugation, capture onto nucleic acid binding solid supports, chromatography or any combination thereof. Conveniently, the probe can be provided on a solid support thereby effecting separation of the amplification product from the remainder of the amplification reaction in a single step. In another embodiment the probe may carry a binding moiety, or the label may be a binding moiety, that will allow manipulation of the probe and any amplification product hybridised thereto. Suitable binding moieties are discussed above.

Preferably any unbound label, e.g. in the form of a labelled oligonucleotide probe, will be separated from the amplification product before the detection step. This can be by any convenient means, for instance with one or more washing steps (e.g. with water or a buffered solution which may contain formamide and/or a detergent), electrophoresis, centrifugation, capture onto solid supports, chromatography or any combination thereof. Suitable solid supports are described above.

If the amplification method used is itself quantitative, e.g. amplification methods in which internal standards and controls are incorporated (for instance qPCR) the method of this aspect of the invention can also provide quantitative data. In these embodiments the method can even affix a numerical value to the amount of target sequence present in the sample and thus the amount of the bacteria containing the target sequence in the sample. One such internal standard would be to amplify one or more (e.g. at least 2, 3, 5, or 10) samples which have known amounts of the bacteria targeted by the oligonucleotides of the probe set or of known quantities of target sequence under the same conditions as the test sample to provide a standard curve plotting amount of amplification product against number of organisms or amount of target sequence. The amount of amplification product obtained in the test sample can then be translated into a numerical value for the amount of target sequence and/or bacteria containing the target sequence of the oligonucleotides of the probe set in the sample.

In other embodiments, the progress of the amplification reaction can be followed in real-time and the amplification profile can be compared with amplification profiles from samples which have known amounts of the bacteria targeted by the oligonucleotides of the probe set or of known quantities of target sequence. In other embodiments the cycle threshold ($C_T$) can be used to calculate the amount of target sequence and therefore the amounts of the bacteria targeted by the oligonucleotides of the probe set in the sample. In all qPCRs there is a threshold at which the fluorescence of the amplification product is detected above background. The cycle at which this threshold is crossed is the $C_T$. In the exponential phase of the reaction the quantity of DNA theoretically doubles every cycle and so relative amounts of DNA can be calculated between samples by comparing $C_T$ values falling in the exponential phase. If the comparison is made with samples with a known quantity of template, the quantity of template in the test sample can be calculated and the amount of target sequence of the oligonucleotides of the probe set present in the sample and thus the amount of bacteria containing the target sequence of the oligonucleotides of the probe set in the sample can be determined A combination of one or more the above described techniques for determining the amount of target nucleotide sequence may be used in the practice of the invention.

The subject may be any human or non-human animal subject, but more particularly may be a vertebrate, e.g. a mammal, including livestock and companion animals. Preferably the subject is a human. The subject may be of any age, e.g. an infant, a child, a juvenile, an adolescent or an adult, preferably an adult. In humans, an adult is considered to be of at least 16 years of age and an infant to be up to 2 years of age. In certain embodiments the subject will be an infant, in others it will be a child or an adult.

The methods of the invention are in vitro methods performed using any sample taken from the GI tract. The GI tract, also referred to as the digestive tract or alimentary canal (and which terms may be used interchangeably with GI tract) is the continuous series of organs beginning at the mouth and ending at the anus. Specifically this sequence consists of the mouth, the pharynx, the oesophagus, the stomach, the duodenum, the small intestine, the large intestine and the anus. These organs can be subdivided into the upper GI tract, consisting of the mouth, pharynx, oesophagus, stomach, and duodenum, and the lower GI tract, consisting of the jejunum, the ileum (together the small intestine), the cecum, the colon, the rectum (together the large intestine) and the anus.

A GI tract sample of use in the invention may include, but is not limited to any fluid or solid taken from the lumen or surface of the GI tract or any sample of any of the tissues that form the organs of the GI tract. Thus the sample may be any luminal content of the GI tract (e.g. stomach contents, intestinal contents, mucus and faeces/stool, or combinations thereof) as well as samples obtained mechanically from the GI tract e.g. by swab, rinse, aspirate or scrape of a GI tract cavity or surface or by biopsy of a GI tract tissue/organ. Faecal samples are preferred. The sample can also be obtained from part of a GI tract tissue/organ which has been removed surgically. The sample may be a portion of the excised tissue/organ. In embodiments where the sample is a sample of a GI tract tissue/organ the sample may comprise a part of the mucosa, the submucosa, the muscularis externa, the adventitia and/or the serosa of the GI tract tissue/organ. Such tissue samples may be obtained by biopsy during an endoscopic procedure. Preferably the sample is obtained from the lower GI tract, i.e. from the jejunum, the ileum, the cecum, the colon, the rectum or the anus. More preferably the sample is a mucosal or luminal sample. Faecal samples may be collected by the swab, rinse, aspirate or scrape of the rectum or anus or, most simply, the collection of faeces after defecation.

The sample may be used in the methods of the invention in the form in which it was initially retrieved. The sample may also have undergone some degree of manipulation, refinement or purification before being used in the methods of the invention. Thus the term "sample" also includes preparations thereof, e.g. relatively pure or partially purified starting materials, such as semi-pure preparations of the above mentioned samples. The term "sample" also includes preparations of the above mentioned samples in which the RNA of which, including the 16S rRNA, has undergone reverse transcription.

The purification may be slight, for instance amounting to no more than the concentration of the solids, or cells, of the sample into a smaller volume or the separation of cells from some or all of the remainder of the sample. Representative cell isolation techniques are described in WO98/51693 and WO01/53525.

In other embodiments the invention uses a preparation of the nucleic acid from the above mentioned samples, preferably a preparation in which the nucleic acids have been labelled. Such preparations include reverse transcription products and/or amplification products of such samples or nucleic acid preparations thereof. Preferably the predominant nucleic acid of the nucleic acid preparation is DNA.

Techniques for the isolation of nucleic acid from samples, including complex samples, are numerous and well known in the art and described at length in the literature. The techniques described in WO98/51693 and WO01/53525 can also be employed to prepare nucleic acids from the above mentioned samples. These preparations include relatively pure or partially purified nucleic acid preparations.

Preferably the amplification reaction performed on the sample will be universal, or substantially universal, in that the nucleic acid to be amplified, i.e. the region of 16S rRNA or 16S rDNA incorporating the above discussed target sequences, is amplified from all, or at least substantially all, prokaryotic cells that might be present in a sample. The term "amplification from substantially all prokaryotic cells present in a sample" refers to the number of different species of prokaryotic cells in the sample that will have the nucleic acid to be amplified, amplified. Thus, in this embodiment the nucleic acid to be amplified is amplified from at least one representative of substantially all species of prokaryotic cells in the sample.

By "prokaryotic cell" it is meant any organism that lacks a cell nucleus, i.e. any organism from the domains Bacteria and Archaea.

Conveniently this universal amplification may be performed using a forward primer targeting the conserved region between V2 and V3 (e.g. that described in Nadkarni et al., 2002. Microbiology 148, 257-266) with a reverse primer targeting the 3'-end of the 16S rRNA gene (e.g. that described in Weisburg et al., 1991, J Bacteriol 173, 697-703). In other embodiments this universal amplification may be performed using a primer pair having the sequences TCC TAC GGG AGG CAG CAG (SEQ ID NO 53), also referred to as MangalaF-1, and CGG TTA CCT TGT TAC GAC TT (SEQ ID NO 54), also referred to as 16SU1510R. This primer pair is described in more detail in US 2011/0104692.

The target nucleotide sequence to be amplified in this embodiment is therefore present in 16S rRNA and the corresponding 16S rRNA gene (rDNA). Thus, reference to the amplification of this target nucleotide sequence is a reference to an increase in the number of nucleic acids that contain that sequence of nucleotides without limitation on the type of nucleic acids containing the nucleotide sequence. Preferably these nucleic acids will be labelled. Typically, the nucleic acid that is formed as the amplification product is DNA, although the nucleotide sequence contained in that nucleic acid will still be the same as that of the target nucleotide sequence, or the complement thereof.

Conveniently, this embodiment of the invention will be performed with 16S rDNA, e.g. a 16S rRNA gene, as the template.

In other embodiments 16S rRNA may be the source of the target nucleotide sequence to be amplified. When a target nucleotide sequence from 16S rRNA is amplified in this embodiment of the method of the invention there will be a step in which an RNA-dependent DNA polymerase catalyses the formation of a DNA molecule complementary to the 16S rRNA template (cDNA). This process is termed "reverse transcription". More specifically the RNA-dependent DNA polymerase catalyses the polymerisation of deoxyribonucleoside triphosphates in a sequence that is complementary (i.e. following Watson-Crick base pairing rules) to a primed template rRNA sequence.

Numerous enzymes have been identified that have the ability to catalyse this reaction and examples include, but are not limited to, HIV reverse transcriptase, AMV reverse transcriptase, M-MLV reverse transcriptase, *C. therm.* polymerase, and Tth polymerase. At its most basic a complete reverse transcription reaction mixture will contain a reverse transcription enzyme, the rRNA template, suitable primers that can bind to the template and from which the reverse transcriptase can begin polymerisation, dNTP's and a suitable buffer. Incubation of the mixture at the working temperature of the reverse transcriptase results in cDNA production.

Upon completion of the reverse transcription reaction the cDNA can be used as the template in the embodiment of the method of the invention described above. The cDNA therefore has a nucleotide sequence that is complementary to the rRNA molecule that was its template. In addition the cDNA has a nucleotide sequence that is the same as a nucleotide sequence contained in one strand of the gene of the rRNA template and the cDNA is complementary to a nucleotide sequence contained in the other strand of the gene of the rRNA template.

As mentioned above, in embodiments of the method of the invention in which nucleic acid is amplified in a preceding step, if 16S rRNA is used as the source of the target nucleotide sequence (as opposed to 16S rDNA, e.g. a 16S rRNA gene) an initial reverse transcription step is required. Reverse transcription linked amplification reactions, in particular PCR, can be "one step" or "two step" processes. In a one step process the components of the reverse transcription reaction and the nucleic acid amplification reaction are present in a single reaction vessel and typically the early reaction conditions are selected to allow the reverse transcription reaction to proceed to completion and reaction conditions are then switched to conditions suitable to allow the nucleic acid amplification reaction to proceed.

In a two step process the components of the reverse transcription reaction are first combined and the reverse transcription reaction is performed. The reverse transcription product is then combined with the components of the amplification reaction and subjected to the amplification reaction. In a "one tube" two step protocol the amplification reaction components are added to the same reaction vessel in which the reverse transcription reaction was performed. In a "two tube" two step protocol the amplification reaction is performed in a fresh reaction vessel.

Many diseases and conditions, or stages thereof, are believed to be linked to characteristic profiles of the microbiota of the GI tract or the microbiota of the regions/parts thereof, e.g. those described above. In some instances the disease or condition may be caused by, or is exacerbated by, perturbations in the profile of the microbiota of the GI tract or of regions/parts thereof. In other instances the disease or condition causes, or by some mechanism results in, the display of a particular profile of the microbiota of the GI tract or of regions/parts thereof. Accordingly, by analysing microbiota profiles in GI tract samples, information can be provided that permits the diagnosis of a disease or condition, or that permits an assessment of the risk of developing a disease or condition, which has been determined to be characterised by a particular microbiota profile. The probe set of the invention may therefore be used to prepare standard microbiota profiles of the GI tract that are characteristic of a disease or condition, or stage thereof, or the risk of developing a disease or condition. The profile may also be of use in disease prognosis and the monitoring of disease.

Thus in another aspect the invention provides a method of preparing a standard microbiota profile of the GI tract that is characteristic of a disease or condition or a stage thereof or the risk of developing a disease or condition, said method comprising:

(i) identifying a subject with said disease or condition or stage thereof or being at risk of developing said disease or condition and contacting a sample from the GI tract of said subject with an oligonucleotide probe set as defined above;

(ii) subjecting the sample and the probe set to conditions which allow hybridisation of the probes to their target nucleotide sequences within nucleic acid molecules in said sample; and (iii) for each oligonucleotide in said probe set, determining the amount of its target nucleotide sequence that is present in said sample.

A profile of the microbiota of the GI tract of the subject is thereby generated from the amounts of the target sequence for each oligonucleotide present in said sample and the profile is characteristic of said disease or condition (or stage thereof) or the risk of developing said disease or condition.

Once a standard profile has been obtained for a particular disease or condition or risk of being developed, typically after the profiling of a plurality of samples from a plurality of subjects with the same disease or condition or stage thereof, this profile may be used as the basis of a diagnostic process to determine whether a further subject is suffering from, or at risk of developing, said disease or condition, or to determine the progress or extent of onset of said disease or condition for prognostic purposes. The standard profile may be provided digitally, e.g. on digital media or via electronic transfer to the user. In other embodiments a system may be in place in which the profile obtained from the subject under test contributes to the development of the standard profile.

In a further aspect the invention provides a method of diagnosing or monitoring a disease or condition in a subject or predicting or assessing the risk of a subject developing a disease or condition, said method comprising:

(a) profiling the microbiota of the GI tract of a subject as described above (b1) comparing said profile to a standard microbiota profile of the GI tract that is characteristic of a disease or condition or a stage thereof or the risk of developing a disease or condition and/or (b2) comparing said profile to an earlier microbiota profile of the GI tract of the subject; and (c) determining the degree of correlation between said profiles.

In this embodiment said degree of correlation is indicative of the presence or absence of said disease or condition, or the risk developing said disease or condition, or the progress of the disease or condition.

In a further aspect the invention also provides a method of diagnosing or monitoring a disease or condition in a subject or predicting or assessing the risk of a subject developing a disease or condition, said method comprising:

(a) comparing the results of a method as described above to a standard microbiota profile of the GI tract that is characteristic of a disease or condition or a stage thereof or the risk of developing a disease or condition and/or (a2) comparing the results of a method as described above to an earlier microbiota profile of the GI tract of the subject, and (b) determining the degree of correlation between said profiles, wherein the degree of correlation is indicative of the presence or absence of said disease or condition, or the risk of developing said disease or condition, or the progress of the disease or condition.

Preferably the profile to which the profile of the subject under test is compared to will be a profile prepared in accordance with the invention. This may be a prepared profile, or could be a profile prepared at the same or substantially the same time as the sample under investigation is being analysed.

"Diagnosis" refers to determination of the presence or existence of a disease or condition or stage thereof in an organism. "Monitoring" refers to establishing the extent of, or possible changes in. a disease or condition, particularly when an individual is known to be suffering from a disease or condition, for example to monitor the effects of treatment or the development of a disease or condition, e.g. to determine the suitability of a treatment, to provide a prognosis, and/or to determine if a patient is in remission or relapse.

"Assessing the risk of a subject developing a disease or condition" refers to the determination of the chance or the likelihood that the subject will develop the disease or condition. This may be expressed as a numerical probability in some embodiments. The assessment of risk may be by virtue of the extent a correlation is seen between the profile of a sample from a subject under investigation and the profile of a disease or condition, or the correlation between the profile of a sample from a subject under investigation and the profile deemed to be characteristic of a sample from a subject determined as having a particular level of risk of developing a disease or condition.

"Disease" refers to a state of pathological disturbance relative to normal which may result, for example, from infection or an acquired or congenital genetic imperfection.

A "condition" refers to a state of the mind or body of an organism which has not occurred through disease, e.g. the presence of an agent in the body such as a toxin, drug or pollutant, or pregnancy.

"Stage thereof" refers to different stages of a disease or condition which may or may not exhibit particular physiological or metabolic changes, but do exhibit changes in the profile of the GI tract microbiota. In some embodiments the observed differences in the profile of GI tract microbiota may lead to a previously unappreciated classification of the progress of a disease or condition.

Data generated using the above mentioned methods may be analysed using various techniques, from the most basic visual representation (e.g. relating to signal intensity) to more complex data manipulation, which may be quantified and expressed mathematically, to prepare the profiles of GI tract microbiota which reflect the interrelationship of the relative levels of each target sequence to which the various probes bind (and thereby the relative levels of bacteria containing the target sequence to which the various probes bind). Conveniently, the raw data thus generated may be manipulated by data processing and statistical methods, particularly normalising and standardising the data, and interrogating the data statistically to determine whether said data reflects the profile of a particular disease, condition or stage thereof. The skilled man would be aware of suitable statistical techniques to use. Preferably the statistical technique will provide a "value" as an indication that the trend being observed is not a random trend. A statistically significant result, i.e. a result that is not attributable to random variation when compared to its control, will have a P value of <0.05, preferably <0.01, <0.005 or <0.001. Merely by way of example, suitable techniques for measuring statistical significance in the methods of the invention are ANOVA, Mann-Whitney-Wilcoxon (MWW) Test, Kruskal-Wallis Test and Tukey's Honestly Significant Differences (HSD) Test. Many others, would be familiar to the skilled man. In some embodiments a permutation test might be appropriate, e.g. that described by Langsrud (2002, Journal Of The Royal Statistical Society Series D 51, 305-317).

The diseases and conditions that may be investigated using the methods of the invention are not limited, although the diagnostic aspects of the invention rely of there being the presence of a consistent profile of GI tract microbiota that is characteristic of the disease or condition under investigation. Diseases and conditions affecting the GI tract are very likely to result in characteristic microbiota profiles, e.g. Inflammatory Bowel Disease (IBD), Crohn's Disease (CD), Ulcerative Colitis (UC), Irritable Bowel Syndrome (IBS) and GI tract cancers (e.g. cancer of the mouth, pharynx, oesophagus, stomach, duodenum, jejunum, ileum, cecum, colon, rectum or anus) and evidence also exists of links between GI tract microbiota and diseases and conditions that are considered to be unrelated to the GI tract, for instance the atopic diseases, e.g. eczema, asthma, atopic dermatitis, allergic conjunctivitis, allergic rhinitis and food allergies; metabolic disorders, e.g. diabetes mellitus (type 1 and type 2), obesity and metabolic syndrome; neurological disorders, e.g. depression, multiple sclerosis, dementia, and Alzheimer's disease; and autism. Any of these diseases or conditions may be diagnosed or monitored in accordance with the invention.

The diagnostic method may be used alone as an alternative to other diagnostic techniques or in addition to such techniques. For example, methods of the invention may be used as an alternative or additional diagnostic measure to diagnosis using imaging techniques such as Magnetic Resonance Imagine (MRI), ultrasound imaging, nuclear imaging, X-ray imaging or endoscopy.

Thus, in a further aspect, the present invention provides a method of obtaining information relevant to the diagnosis or monitoring of a disease or condition or the assessment of the risk of developing a disease or condition which comprises a method of profiling the microbiota of the GI tract of a subject as defined above.

In a further aspect the invention provides kits comprising the probe set as defined herein.

In a further aspect the invention provides the use of the probe set defined herein in the manufacture of the kits as defined herein.

The kits of the invention may be designed for use in the methods of the invention and may comprise further components. Each component may be provided in a separate compartments or vessels. Where convenient and practical, mixtures of components could be provided. The components may be provided in dry, e.g. crystallised, freeze dried or lyophilised, form or in solution, typically such liquid compositions will be aqueous and buffered with a standard buffer such as Tris, HEPES, etc.

The kit may also be provided with instructions for using the kit, or with directions for how instructions may be obtained.

The additional components can be any of the various components that may be used to put the methods of the invention into effect, e.g. any component discussed above. In a preferred embodiment the kit further comprises means for selective labelling of the oligonucleotide probes. In a preferred embodiment the kit further comprises suitable solid supports on which the oligonucleotides of the probe set of the invention may be immobilised, e.g. any of those solid supports described herein. In other embodiments some or all of the oligonucleotides of the probe set of the invention are supplied in the kit in immobilised form.

Further components might optionally be any or all of the means, e.g. buffers, enzymes etc. for performing an amplification and/or primer extension reaction with the oligonucleotides of the invention. For instance, the kits may optionally contain a PCR reaction buffer, nucleotide triphosphates, further oligonucleotide primers, or DNA polymerases, preferably a thermostable polymerase such as Taq polymerase.

Further components might optionally be any or all of the means, e.g. buffers, enzymes etc. for performing a reverse transcription reaction. For instance a reverse transcriptase, RNA specific primers, an RT reaction buffer, and nucleotide triphosphates.

Further components might optionally be any or all of the means to take the sample. For instance such means might include dipsticks, biopsy apparatus, swabbing devices, pouches or vessels. Preferably these means will be provided in sterile form.

Further components might optionally be any or all of the means to purify or refine the sample. For instance means to isolate or concentrate cells in a sample, e.g. cell binding solid supports or filtration devices. In other embodiments the means to purify or refine the sample might be any or all of the means for extracting nucleic acid from a sample. For instance cell lysis reagents (e.g. chaotropic salts, alcohols, detergents, membrane altering compounds), nucleic acid binding solid supports (e.g. as described above) or nucleic acid precipitating agents (e.g. salts, alcohols)

Further components might optionally be any or all of the means to detect amplified nucleic acid. For instance the labels described herein (e.g. double stranded DNA binding dyes, labelled oligonucleotide probes), apparatus to detect these labels, electrophoresis materials and apparatus, or chromatography materials and apparatus.

Further components might optionally be further oligonucleotides that selectively hybridise to target nucleic acids indicative of any other disease or medical condition, particularly conditions associated with the gastrointestinal microbiota (e.g. CD, IBS, UC, IBD) and which may accordingly be used in a manner similar to the oligonucleotides of the invention to provide information relevant to a diagnosis of any other disease of medical condition, particularly conditions associated with the gastrointestinal microbiota (e.g. CD, IBS, UC, IBD). These oligonucleotides may be considered a part of the probe set of the invention.

The invention will be further described with reference to the following non-limiting Examples in which:

FIG. 1 shows the temporal development of bacterial phyla in sensitized and non-sensitized infants. Log average signal for each probe is shown as full line, while log signal of all time points measured are shown as dots (levels above a signal threshold of 50, denoted by stippled lines). Dark grey lines and dots are for sensitized children, while light grey lines and dots are for non-sensitized children. Values<0 are set to 0.001 before log transformation.

Figure 2:
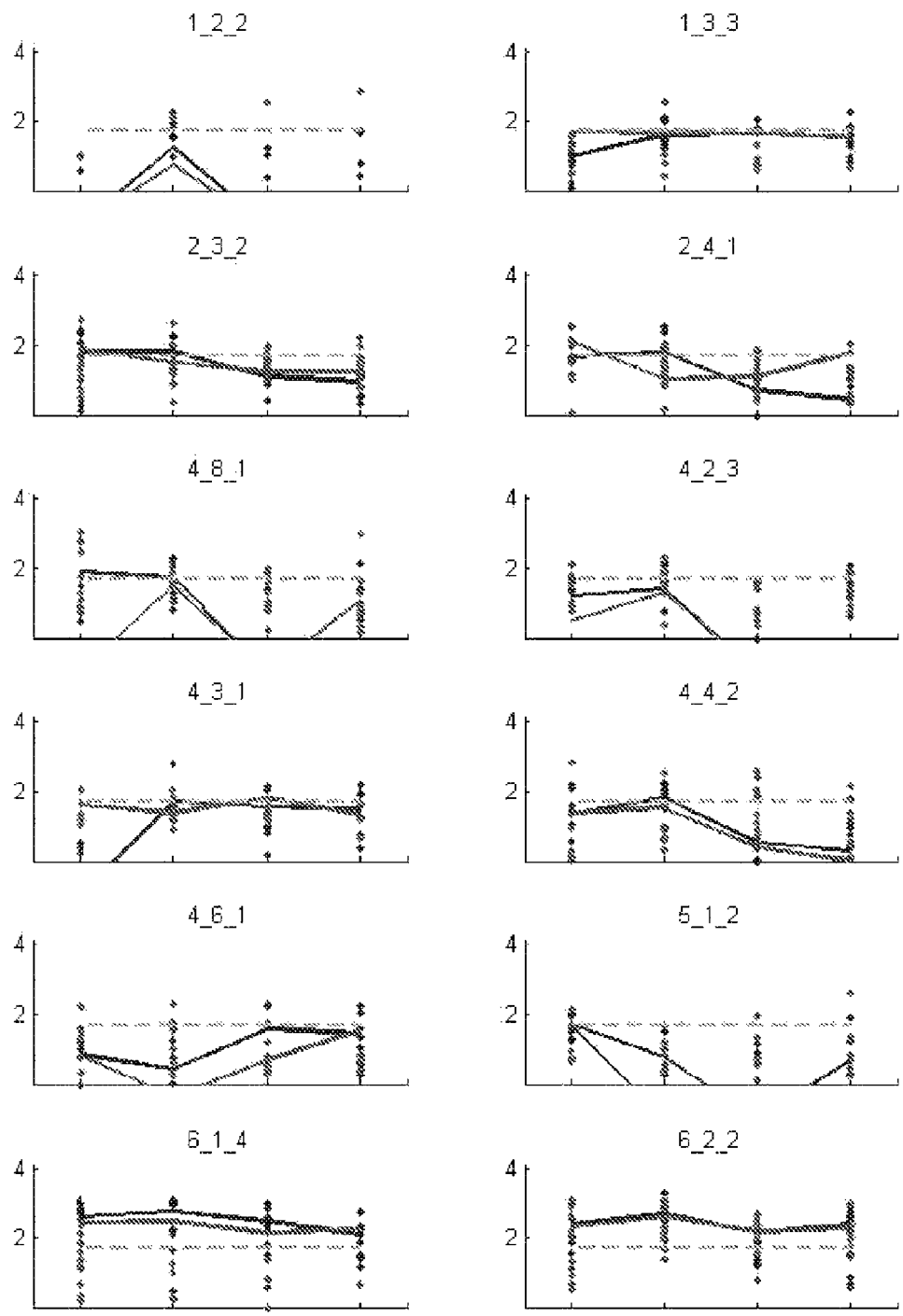

FIG. 2 shows the temporal development of bacterial genera/species in sensitized and non-sensitized infants. Log average signal for each probe is shown as full line, while log signal of all time points measured are shown as dots (levels above a signal threshold of 50 are denoted by stippled lines). Dark grey lines and dots are for sensitized children, while light grey lines and dots are for non-sensitized children. Values<0 are set to 0.001 before log transformation. Probes with maximum signal below the threshold are not shown.

TABLE 1

| Probe sequence | SEQ ID NO | Target bacteria (general description) |
|---|---|---|
| TTGCGGCTCAACCGTAAAATTG | SEQ ID NO 5 | *Bacteroides* |
| CAATTTTACGGTTGAGCCGCAA | SEQ ID NO 31 | *Bacteroides* |
| GCACTCAAGACATCCAGTATCAACTG | SEQ ID NO 6 | *Bacteroides* (*dorei, fragilis, thetaiotaomicron, vulgatus*) |
| CAGTTGATACTGGATGTCTTGAGTGC | SEQ ID NO 32 | *Bacteroides* (*dorei, fragilis, thetaiotaomicron, vulgatus*) |
| AGGGCAGTCATCCTTCACG | SEQ ID NO 7 | *Bacteroides* (*dorei, fragilis, thetaiotaomicron, vulgatus*) |
| CGTGAAGGATGACTGCCCT | SEQ ID NO 33 | *Bacteroides* (*dorei, fragilis, thetaiotaomicron, vulgatus*) |
| CAATCGGAGTTCTTCGTGATATCTAAG | SEQ ID NO 8 | *Bacteroides* |
| CTTAGATATCACGAAGAACTCCGATTG | SEQ ID NO 34 | *Bacteroides* |

TABLE 2

| Probe sequence | SEQ ID NO | Target bacteria (general description) |
|---|---|---|
| TGTTGTGGTTAATAACCGCAGCAATTGA | SEQ ID NO 9 | *Salmonella, Enterobacter, Citrobacter, Cronobacter* |
| TCAATTGCTGCGGTTATTAACCACAACA | SEQ ID NO 35 | *Salmonella, Enterobacter, Citrobacter, Cronobacter* |
| TCCAATGACCCTCCC | SEQ ID NO 10 | *Enterococcus, Listeria* |
| GGGAGGGTCATTGGA | SEQ ID NO 36 | *Enterococcus, Listeria* |
| CACTCTCACACCCGTT | SEQ ID NO 11 | *Streptococcus sanguinis* |
| AACGGGTGTGAGAGTG | SEQ ID NO 37 | *Streptococcus sanguinis* |
| GTTGCTCGGTCAGACTT | SEQ ID NO 12 | *Streptococcus, Enterococcus* |
| AAGTCTGACCGAGCAAC | SEQ ID NO 38 | *Streptococcus, Enterococcus* |
| CGTGGCTTTCTGATTAGGTA | SEQ ID NO 13 | *Staphylococcus* |
| TACCTAATCAGAAAGCCACG | SEQ ID NO 39 | *Staphylococcus* |
| TGCTTATTCAACGGGTAAACT | SEQ ID NO 14 | *Bifidobacterium longum* |
| AGTTTACCCGTTGAATAAGCA | SEQ ID NO 40 | *Bifidobacterium longum* |
| CCGTCACTCGGCTACCATTTC | SEQ ID NO 15 | *Clostridium ramosum* |
| GAAATGGTAGCCGAGTGACGG | SEQ ID NO 41 | *Clostridium ramosum* |
| GATTTTCCACTCCCACCAT | SEQ ID NO 16 | *Streptococcus pyogenes* |
| ATGGTGGGAGTGGAAAATC | SEQ ID NO 42 | *Streptococcus pyogenes* |
| CCGTCAAGGGACAAG | SEQ ID NO 17 | *Listeria monocytogenes* |
| CTTGTCCCTTGACGG | SEQ ID NO 43 | *Listeria monocytogenes* |
| CGGTGCTTATTCGAAAGGTACACT | SEQ ID NO 18 | *Bifidobacterium. breve* |
| AGTGTACCTTTCGAATAAGCACCG | SEQ ID NO 44 | *Bifidobacterium. breve* |

TABLE 3

| Probe sequence | SEQ ID NO | Target bacteria (general description) |
|---|---|---|
| CGCCTGCCTCAAACATA | SEQ ID NO 19 | Parabacteroides |
| TATGTTTGAGGCAGGCG | SEQ ID NO 45 | Parabacteroides |
| CAGGTGTAGCGGTGAAATGCGTAGAGAT | SEQ ID NO 20 | Gamma-proteobacteria |
| ATCTCTACGCATTTCACCGCTACACCTG | SEQ ID NO 46 | Gamma-proteobacteria |
| ACGCTCGCACC | SEQ ID NO 21 | Haemophilus |
| GGTGCGAGCGT | SEQ ID NO 47 | Haemophilus |
| CGGGGATTTCACATCTGA | SEQ ID NO 22 | Gamma-proteobacteria subgroup |
| TCAGATGTGAAATCCCCG | SEQ ID NO 48 | Gamma-proteobacteria subgroup |
| TGCCAGTTTCGAATGCAGTT | SEQ ID NO 23 | Gamma-proteobacteria subgroup |
| AACTGCATTCGAAACTGGCA | SEQ ID NO 49 | Gamma-proteobacteria subgroup |
| GTGCTTCTTCTGCGGGTAA | SEQ ID NO 24 | Gamma-proteobacteria subgroup |
| TTACCCGCAGAAGAAGCAC | SEQ ID NO 50 | Gamma-proteobacteria subgroup |
| GCTACACATGGAGTTCCA | SEQ ID NO 25 | Lactobacillus subgroup |
| TGGAACTCCATGTGTAGC | SEQ ID NO 51 | Lactobacillus subgroup |
| CGTAGTTAGCCGTGG | SEQ ID NO 26 | Clostridium neonatale |
| CCACGGCTAACTACG | SEQ ID NO 52 | Clostridium neonatale |

EXAMPLE 1

The aim of the present work was to prospectively compare the development of the dominant microbiota in IgE sensitised children and non-sensitised children during the two first years of life. In order to accomplish this and other gut microbiota related tasks, a tool to rapidly screen for the complexity and composition of the bacteria in stool samples was needed. We therefore developed an infant high-throughput 16S rRNA gene microarray, called GA-map infant assay. The microarray analyses were performed on a selected subset of the IM-PACT cohort. Specific IgE was chosen as an atopy marker, since we have previously shown that this marker is correlated to gut bacteria (unpublished results).

The main difference between GA-map infant array and alternative 16S rRNA gene array approaches is the use of highly specific single nucleotide primer extension (SNuPE) probes for target/non-target discrimination. The high specificity of the SNuPE assay is obtained by DNA polymerase based incorporation of a fluorescently labelled dideoxynucleotide. The SNuPE probes are constructed so that the probes hybridize adjacent to discriminative gene positions. To reduce complexity and to increase throughput, the GA-map infant assay was targeted to bacteria expected to colonize the infant gut. The probes were selected based on the criterion of the minimum number of probes covering the expected diversity of bacteria in the infant gut.

Materials and Methods

Cohort

The Prevention of Allergy Among Children in Trondheim (PACT) study is a large population based intervention study in Norway focused on childhood allergy. The samples included here are a subset from the PACT study, where we undertook immunology and microbiology measurements. For the sub-study family doctors and midwives in Trondheim participated in recruiting an unselected population of women during ordinary early pregnancy check-ups until 720 had approved to participate. The women filled in questionnaires on risk factors during pregnancy, at six weeks after delivery, at one and two years after giving birth. The questions were on allergy in the family, housing conditions, diet and lifestyle, and after birth on breastfeeding, food supplements, diet, infections, vaccines, antibiotics, stays in day-care centres and nicotine exposure. When the infants turned two years, another questionnaire on health and disease was submitted. Atopic sensitization was assessed as elevated specifics IgE ($\geq 0.35$ kU/ml) in serum using an assay for a range of allergens (Immulite 2000 Allergen-specific IgE system, Siemens Medical Solutions Diagnostics). The cohort was initially analyzed for twelve specific bacteria by quantitative PCR (unpublished results). Here, we selected a range of infants for in-depth GA-map infant array testing based on number of samples, and sensitization state. A total of 16 sensitized and 31 non-sensitized children were selected, representing a total of 216 faecal samples.

Sample Preparation and PCR Amplification

Faeces were collected from the napkin and transferred to a Carry Blair transport media by the parents, stored immediately at −18° C. at home before transported to permanent storage at −80° C. until further analysis. Mechanical lysis was used for cell disruption, and an automated magnetic bead-based method was used for DNA purification.

We combined the use of a forward primer targeting the conserved region between V2 and V3 (Nadkarni et al., 2002.

Microbiology 148, 257-266.) with a reverse primer targeting the 3'-end of the 16S rRNA gene (Weisburg et al., 1991, J Bacteriol 173, 697-703). We used 1.5 U HotFirePol (Solis Biodyne, Tartu, Estonia), 1×B2 buffer (Solis Biodyne), 2.5 mM $MgCl_2$ (Solis Biodyne), 200 μM dNTP (Thermo Fisher Scientific, Waltham, USA), 0.2 μM of each forward and reverse primer and approximately 10 to 50 ng template in a total volume of 25 μl. One of the samples was amplified three times to examine the reproducibility of the PCR-reaction (described in further detail under the Capillary Electrophoresis section). The amplification protocol included a 15 min activation stage at 95° C., followed by 30 cycles with 30 sec denaturation at 95° C., 30 sec annealing at 55° C. and 90 sec extension at 72° C. A final elongation for 7 min at 72° C. was included for completion of all the PCR products.

For the initial tests of the array, 16S rRNA gene PCR was performed on bacterial DNA from pure cultures of 26 strains listed in Table 4, and the PCR products were tested in the down-stream GA-map infant assay. The strains were sequenced to confirm their identity and possible mutations (sequence accession numbers are listed in Table 4). A positive control consisting of a mixture of DNA from pure cultures of 8 relevant bacterial strains as well as a negative control consisting of $H_2O$ was included during the 16S rRNA gene PCR reaction and the down-stream GA-map infant assay. The positive controls were used as a quality control of the labelling reaction and hybridization of the arrays (results not shown).

Design of the GA-Map Infant Assay

The GA-map assay is based on the single nucleotide extension principle (SNupE) in combination with microarray hybridization (Rudi et al., 1998, Appl Environ Microbiol 64, 2639-2643)

The bacterial strains shown in Table 4 were used for probe validation. For probe construction we used a combined dataset consisting of a total of 3580 16S rRNA gene sequences (Palmer et al., 2007, PLoS Biology 5, e177; Rudi et al., 2007, Appl Environ Microbiol 73, 2727-2734), in addition to a set of known pathogens.

TABLE 4

Bacterial strains used for probe evaluation

| Class | Species | Strain | Accession # |
|---|---|---|---|
| Actinobacteria | Bifidobacterium breve | DSM20213 | HQ012023 |
| | Bifidobacterium longum subsp. infantis | DSM20088 | HQ012021 |
| | Bifidobacterium longum subsp. longum | DSM20219 | HQ012022 |
| Bacteroidetes | Bacteroides dorei | DSM17855 | HQ012025 |
| | Bacteroides fragilis | DSM2151 | HQ012027 |
| | Bacteroides thetaiotaomicron | DSM2079 | HQ012026 |
| | Bacteroides vulgatus | DSM1447 | HQ012024 |
| | Parabacteroides distasonis | DSM 20701 | N/A |

TABLE 4-continued

Bacterial strains used for probe evaluation

| Class | Species | Strain | Accession # |
|---|---|---|---|
| Firmicutes | Clostridium perfringens | DSM756 | HQ012013 |
| | Clostridium ramosum | DSM1402 | HQ012012 |
| | Enterococcus faecalis | DSM20478 | HQ012029 |
| | Enterococcus faecium | DSM20477 | HQ012007 |
| | Lactobacillus acidophilus | DSM20079 | HQ012028 |
| | Lactobacillus rhamnosus | DSM20021 | HQ012008 |
| | Listeria monocytogenes | DSM20600 | HQ012006 |
| | Staphylococcus aureus subsp. aureus | DSM20231 | HQ012011 |
| | Streptococcus pneumoniae | DSM20566 | HQ012009 |
| | Streptococcus pyogenes | DSM20565 | HQ012030 |
| | Streptococcus sanguinis | DSM20567 | HQ012010 |
| | Veillonella atypical | DSM20739 | HQ012015 |
| | Veillonella dispar | DSM20735 | HQ012014 |
| Proteobacteria | Escherichia coli | DSM30083 | HQ012019 |
| | Haemophilus parainfluenzae | DSM8978 | HQ012020 |
| | Klebsiella pneumoniae subsp. pneumoniae | DSM30104 | HQ012018 |
| | Salmonella bongori | DSM13772 | HQ012016 |
| | Salmonella enterica subsp. enterica | DSM17058 | HQ012017 |

We used a four-step process in designing the probes. 1) First, we defined a set of target and non-target groups based on a coordinate classification system. 2) The next step was to identify probes that satisfy the criteria of target detection and non-target exclusion. This was based on a combined criterion of hybridization and labelling. All probes were designed with minimum Tm of 60° C. for the target group, while the non-target should have a Tm of <30° C., or the absence of a cytosine as the nucleotide adjacent to the 3'-end of the probe. All probes satisfying the criteria were identified. 3) Then the potential cross-labelling or self-labelling probes were evaluated, in addition to the potential for cross hybridization on the array. 4) Finally, by combining the knowledge about target/non-target groups and compatibility for each of the probes final arrays were designed using a hierarchical approach.

A universal 16S rRNA gene probe (UNI01) was included in the probe sets to measure the total abundance of bacterial DNA in the sample. One additional probe was added in the hybridization step: a 1:4 mixture of pre-labelled and unlabeled hybridization control probe (HYC01). HYC01 is used to measure efficiency of the hybridization step on the slide and to normalize the probe signals between slides. The microarrays used in the GA map infant assay were produced by ArrayIt (ArrayIt, Sunnyvale, USA). One glass slide contains 24 separate identical microarrays, and the probes (complementary to the probes listed in Table 5) were spotted in triplicates on each array. Furthermore, the arrays also included two non-binding control probes (NBC01, NBC02) (Sanguin et al., 2006, Environmental Microbiology 8, 289-307).

TABLE 5

Probes included in Probe Set 3

| Probe ID | Taxonomic groups detected | Probe sequence | False +ve/ false -ve | SEQ ID NO | Mean correct signal | Std correct signal |
|---|---|---|---|---|---|---|
| 1_1 | Bacteroides | TTGCGGCTCAACCGTAAAATTG | 0%/0% | 5 | 1723.54 | 245.51 |
| 1_1_3 | Parabacteroides | CGCCTGCCTCAAACATA | 0%/0% | 19 | 733.62 | N/A |
| 1_2_2 | Bacteroides (dorei, fragilis, thetaiotaomicron, vulgatus) | GCACTCAAGACATCCAGTATCAACTG | 0%/0% | 6 | 1261.71 | 435.04 |

TABLE 5-continued

Probes included in Probe Set 3

| Probe ID | Taxonomic groups detected | Probe sequence | False +ve/ false -ve | SEQ ID NO | Mean correct signal | Std correct signal |
|---|---|---|---|---|---|---|
| 1_3_3 | Bacteroides (dorei, fragilis, thetaiotaomicron, vulgatus) | AGGGCAGTCATCCTTCACG | 0%/0% | 7 | 1157.96 | 391.09 |
| 2_1_min1b | Gamma-proteobacteria | CAGGTGTAGCGGTGAAATGCGTAGAGAT | 14%/0% | 20 | 270.16 | N/A |
| 2_1_1 | Haemophilus | ACGCTCGCACC | 0%/0% | 21 | 1711.24 | 201.24 |
| 2_3_2 | Gamma-proteobacteria subgroup | CGGGGATTTCACATCTGA | 8%/0% | 22 | 141.42 | N/A |
| 2_4_1 | Gamma-proteobacteria subgroup | TGCCAGTTTCGAATGCAGTT | 4%/0% | 23 | 1677.81 | 251.28 |
| 2_5_1 | Gamma-proteobacteria subgroup | GTGCTTCTTCTGCGGGTAA | 0%/0% | 24 | 611.51 | 155.12 |
| 2_7_1 | Salmonella, Enterobacter, Citrobacter, Cronobacter | TGTTGTGGTTAATAACCGCAGCAATTGA | 4%/0% | 9 | 1527.71 | N/A |
| 3_2 | Proteobacteria | ACGCTTGCACCCT | 5%/0% | 1 | 809.64 | 278.90 |
| 4_1 | Firmicutes (Lactobacillales, Clostridium perf, Staphylococcus) | CGATCCGAAAACCTTCTTCACT | 6%/0% | 2 | 1799.51 | 538.14 |
| 4_2_3 | Lactobacillus subgroup | GCTACACATGGAGTTCCA | 29%/0% | 25 | 278.64 | 14.67 |
| 4_3_1 | Clostridium ramosum | CCGTCACTCGGCTACCATTTC | 0%/0% | 15 | 2429.10 | N/A |
| 4_4_2 | Enterococcus, Listeria | TCCAATGACCCTCCC | 0%/0% | 10 | 640.06 | 125.05 |
| 4_5_2 | Streptococcus pyogenes | GATTTTCCACTCCCACCAT | 0%/0% | 16 | 1556.65 | N/A |
| 4_6_1 | Streptococcus sanguinis | CACTCTCACACCCGTT | 0%/0% | 11 | 978.28 | N/A |
| 4_7_2 | Listeria | CCGTCAAGGGACAAG | 0%/0% | 17 | 678.60 | N/A |
| 4_8_1 | Streptococcus Enterococcus | GTTGCTCGGTCAGACTT | 12%/0% | 12 | 1593.28 | N/A |
| 5_1 | Firmicutes (Clostridia, Bacillales, Enterococcus, Lactobacillus) | GGACAACGCTTGCCAC | 6%/0% | 3 | 1315.09 | 417.36 |
| 5_1_2 | Staphylococcus | CGTGGCTTTCTGATTAGGTA | 0%/0% | 13 | 654.06 | N/A |
| 5_2_1 | Clostridium neonatale | CGTAGTTAGCCGTGG | 0%/0% | 26 | 0.00 | 0.00 |
| 6_1_4 | Bifidobacterium longum | TGCTTATTCAACGGGTAAACT | 0%/0% | 14 | 2071.50 | 492.05 |
| 6_2 | Actinobacteria | CGTAGGCGGTTCGTCGCGT | 0%/0% | 4 | 1417.55 | 243.38 |
| 6_2_2 | Bifidobacterium. breve | CGGTGCTTATTCGAAAGGTACACT | 0%/0% | 18 | 1928.16 | N/A |
| UNI01 | 16S Universal | CGTATTACCGCGGCTGCTGGCA | N/A | 55 | N/A | N/A |
| HYC01 | Hybridization control | GTAGCATTCGATTCGGGCAA | N/A | 56 | N/A | N/A |

Primer Extension and Hybridisation to Array

Before the labelling reaction the 16S PCR-products (amplified as described above) were treated with 3U Exonuclease I (New England Biolabs, Ipswich, USA) and 8U Shrimp Alkaline Phosphatase (USB, Cleveland, USA) at 37° C. for 2 hours and inactivated at 80° C. for 15 min. The ExoSAP treated PCR-products were then quantified using Kodak Molecular Imaging Software (Version 4.0) based on pictures from gel electrophoresis. A 1 kB DNA Ladder (N3232, New England Biolabs) with specified concentrations was included on all gels. Based on the quantification from the gel images the PCR products were diluted to an equal concentration of 50 ng/μl per sample and approximately 100 ng template was used in the following labeling reaction: In a total reaction volume of 10 μl 2.5 U HOT TERMIPol (Solis Biodyne), 1× buffer C (Solis Biodyne), 4 mM $MgCl_2$ (Solis Biodyne), 0.4 μM ddCTP-tamra (Jena Bioscience, Jena, Germany) and 2.9 μM probe set 3 (Table 5). The labelling protocol included a 12 mM activation stage at 95° C., followed by 10 cycles with 20 sec denaturation at 96° C. and 35 sec annealing at 60° C. Forty four samples were randomly picked to examine reproducibility. These 44 samples were processed twice starting from the labelling reaction. Furthermore, as a test of the quantitative range of the assay PCR-products from pure cultures from 5 different species (listed in Table 4) was diluted from $10^0$-$10^4$ and included in the labelling reaction and down-stream array analysis.

The arrays were pre-hybridized to prevent background signal by soaking the glass-slides in BlockIt (ArrayIt) at room temperature. After two hours the slides where washed for 2 mM in a wash buffer containing 2×SSC (Sigma-Aldrich, St. Louis, USA)+0.1% Sarkosyl (RT) (VWR, International Ltd., Poole, United Kingdom) and then for 2 mM in 2×SSC (Sigma-Aldrich). The slides were then placed in a beaker with ultra pure H$_2$O (100° C.) for 2 mM and immediately transferred to a beaker containing 100% ethanol (−20° C.) for 20 sec, before they were dried by centrifugation at 91 G in a Multifuge 3 S-R centrifuge (Heraeus, Buckinghamshire, United Kingdom) for 12 min and used within an hour.

Immediately prior the actual array hybridization 60 µl hybridization buffer containing 7.2% Polyethylene glycol 8000 (Sigma-Aldrich), 1.2×SSC (Sigma-Aldrich) and 0.17 µM of the hybridization control probe HYC01 mixture (1:4 mix of tamra labelled HYC01 and unlabeled HYC01) were added to the samples. The samples were denatured at 95° C. for 2 mM and then left at 45° C. for 2 mM The glass-slides were placed in a 96-well hybridization chamber (ArrayIt) before the samples were loaded onto the arrays. Two arrays per slide were used for the positive and negative control samples. The hybridization chamber was placed in a humid chamber and hybridized for 16 hours in an Innova 4000 incubator shaker (New Brunswick Scientific, Champaign, USA) at 45° C. and 60 rpm.

After hybridization the arrays were washed for 5 minutes in the wash buffer containing 2×SSC (Sigma-Aldrich) and 0.1% Sarkosyl (VWR, International Ltd.), then for 5 min in 2×SSC (Sigma-Aldrich) and finally for 10 sec in 0.2×SSC (Sigma-Aldrich), before they were dried by centrifugation at 91 G for 12 min in a Multifuge 3 S-R centrifuge (Heraeus). Hybridized arrays were scanned at wavelength 532 nm with a Tecan LS reloaded scanner (Tecan, Mannedorf, Austria). Fluorescent intensities and spot morphologies were analyzed using Axon GenePix Pro 6.0.

Capillary Electrophoresis

To test the probe specificity, single probes were tested against their target bacteria (DNA from pure cultures) by performing 16S PCR amplification and labelling reactions as described above (with 1 µM of single probes instead of Probe Set 3) and the performance of the probes were evaluated using capillary electrophoresis. Reproducibility of the 16S rRNA gene PCR was examined on one of the samples (amplified in three separate PCR reactions) using capillary electrophoresis. Two probes (6_1_4 and 5_1_2) were chosen to examine the signal for each of the three PCR products, and also a triplicate run on a pool of the three PCR products were examined using the same probes. After labelling, the samples were treated with 8U SAP (USB) and incubated at 37° C. for 1 hour and inactivated at 80° C. for 15 min. Then 1 µl of the SAP-treated and labeled probes were mixed with 9 µL of Hi-Di formamide (Applied Biosystems, Warrington, United Kingdom) and 0.5 µL GeneScan 120 Liz Size Standard (Applied Biosystems), and the samples were incubated at 95° C. for 5 min, and immediately put on ice. The samples were then loaded onto a 50 cm 3130×1 capillary array (Applied Biosystems) in the ABI Genetic Analyzer 3130×1 sequencer (Applied Biosystems), containing the performance optimized polymer 7 (POP-7, Applied Biosystems). Injection time was 16-22 s and the electrophoretic conditions were: run time 1,500 s at 15,000 V, run current 100 µA and 60° C. run temperature. The GeneMapper 4.0 software was used to analyze the results.

The 16S rRNA gene PCR products from the 26 bacterial strains used to evaluate the probes were sequenced to confirm their identity and to examine if there were any mutations in their gene sequences compared to the sequences used to design the probes. The ExoSAP treated PCR products were diluted 10 fold and 1 µl was used in the sequencing reaction using the BigDye® Terminator v1.1 Cycle Sequencing Kit (Applied Biosystems). 0.32 µM of the same forward and reverse primers used for the 16S rRNA PCR described above were used in two separate sequencing reactions. BigDye XTerminator® Purification Kit (Applied Biosystems. Warrington, United Kingdom) was used according to the manufacturer's recommendations to clean up the sequencing reactions. The samples were analyzed on a 36 cm 3130×1 capillary array (Applied Biosystems) in the ABI Genetic Analyzer 3130×1 sequencer (Applied Biosystems), containing the performance optimized polymer 7 (POP-7, Applied Biosystems). Injection time was 3 s and the electrophoretic conditions were: run time 2780 s at 8,500 V, run current 5.0 µA and 60° C. run temperature. The sequences were base called by Sequence Scanner Software v1.0 (Applied Biosystems). The sequences have been deposited to GenBank and the strains respective accession numbers are listed in Table 4.

Data Preprocessing and Analysis

Probe signals were corrected for undesired hybridization variations that are observed from slide to slide. In each experiment, a probe that is already labelled (HYC01) is added to the probe mixture to evaluate the hybridization step. To correct for varying hybridization between slides, we divide all sample signals on the average signal of all replica from this probe. In addition, background signal from each individual probes was removed by subtracting the average signals from a negative control sample included on all slides used in this experiment.

A Neighbour Joining tree of all 26 bacterial strains used to evaluate the probes was constructed using program Mega 4 and its reliability was inferred using bootstrapping.

Statistical Analyses

The probe specificity was evaluated by comparing the theoretical target/non-target values with the experimental results on single-strains, using an empirically determined background signal threshold value of 50.

Microarray data usually contain both threshold and saturation values and are therefore very seldom normally distributed. Thus, in order to test significance of microarray data, it is common to use permutation based approaches instead of standard statistical tests such as ANOVA and t-tests (which require normal distribution). Permutation testing is an exact statistical test, even for data with a complex distribution structure. Hence, the p-values for group differences within each age category were calculated by permutation testing (Langsrud, 2002, Journal Of The Royal Statistical Society Series D 51, 305-317) using 50 as the background threshold value.

Results

Probe Construction and Evaluation

A set of 88 probes were constructed based on the criteria described in Materials and Methods. Six probes for the main phyla covered 88% of the clones in our dataset. Single probe evaluations using capillary gel electrophoresis and the strains in Table 4 as templates showed that 76% of the probes satisfy the criterion of target detection, indicating a relatively high success rate. Based on these results and a set of bioinformatics criteria we identified 10 probe sets. Each probe set consisted of 25 probes which were selected based on their in silico compatibility with each other. The compatibility estimations were based on melting temperature calculations and thermodynamics of the probe—self-hybridization, hybridization to other probes in the probe set or their target bacteria. Experimental validation by capillary gel electrophoresis showed that Probe Set 3 gave the lowest cross-reaction, as determined by labelling without template (results not shown). This probe set was therefore selected for array construction (Table 5).

Specificity, Reproducibility and Quantitative Range of the GA-Map Infant Array

The first evaluation of the array was on pure strains. The evaluation was based on comparing in silico determined target/non-targets with that of experimental signals. This analysis showed good concordance between the theoretical and experimental probe specificities. Using a signal cutoff value of 50 rfu we found that there were no false negatives, while the number of false positives were rather variable (Table 5).

The next step in the evaluation was to determine the classification accuracy of mixed samples. This was done by analyzing a set of defined mixes. The evaluation of these data showed that the majority of the probes accurately identified their target bacteria. Here, we used a threshold signal of 50. In total, there were 96.5% correct with 9.0% false positives and 1.6% false negatives. The quantitative range of the selected probes was subsequently evaluated by template dilutions. In general, these analyses showed that there was a saturation of the probe signal when the target concentration was >10% relative to the undiluted PCR product. All the evaluated probes also gave the same approximate detection limit between 0.1 and 0.01%. The quantitative accuracy was also very high with a $R^2 > 0.9$ for all the probes tested. The reproducibility of the assay was evaluated by duplicate analyses of 43 samples. Mean percentage variation and $R^2$ for each probe individually was determined and confirmed the reproducibility of the assay.

Phylum Level Development of the Gut Microbiota

We found that Actinobacteria (probe 6_2) and Firmicutes (probe 5_1) were significantly overrepresented at 4 months and one year, respectively, in the IgE sensitized children (Table 6 and FIG. 1). There was also an overall consistent age-specific colonization pattern at the phylum level, irrespective of the sensitization state. The general pattern was an initial dominance of Firmicutes and Proteobacteria at ten days. At four months the Proteobacteria/Firmicutes dominance was replaced with Bacteroides/Actinobacteria, while after one and two years the initially colonizing phyla were apparently becoming low in abundance.

TABLE 6

Phylum level differences between sensitized and non-sensitized children at different ages[1]

| Probe | 10 days | 120 days | 360 days | 720 days |
|---|---|---|---|---|
| 1_1 | 0.640 | 0.868 | 1.00 | 0.903 |
| 2_1_min1b | 0.760 | 0.220 | 0.801 | 0.542 |
| 3_2 | 0.922 | 0.3126 | 0.126 | 0.465 |
| 4_1 | 0.164 | 0.190 | 0.360 | 0.599 |
| 5_1 | 0.486 | 0.127 | 0.049 | 0.556 |
| 6_2 | 0.152 | 0.042 | 0.196 | 0.989 |
| UNI01 | 0.450 | 0.867 | 0.917 | 0.216 |

[1]Significance of differences were determined by permutation testing. Significant differences (p < 0.05) are boldfaced.

Genus and Species Level Development of the Gut Microbiota

The main difference between the sensitized and non-sensitized group was that *B. longum* (probe 6_1_4) was significantly overrepresented in the sensitized group, as compared to the non-sensitized group at one year. We also found that Enterococcus (probe 4_4_2) was significantly overrepresented at four months. It also seems like streptococci are associated with sensitization, with *Streptococcus sanguinis* (probe 4_6_1) being significantly overrepresented at one year, and *S. pneumonia* (probe 4_8_1) at border of significance at 10 days (Table 7 and FIG. 2).

The bacterial groups with the most consistent colonization patterns correlating with age were *Staphylococcus* (probe 5_1_2) and *Bifidobacterium breve* (probe 6_2_2). *Staphylococcus* dominated initially, while *B. breve* had a dominance peak at 4 months.

TABLE 7

Genus/species differences between sensitized and non-sensitized children at different ages[1]

| Probe | 10 days | 120 days | 360 days | 720 days |
|---|---|---|---|---|
| 1_1_3 | 1 | 0.866 | 1.000 | 1.000 |
| 1_2_2 | 1 | 0.884 | 1.000 | 1.000 |
| 1_3_3 | 0.756 | 0.488 | 0.206 | 0.741 |
| 2_1_1 | 0.783 | 1.000 | 1.000 | 1.000 |
| 2_3_2 | 0.668 | 0.347 | 1.000 | 0.494 |
| 2_4_1 | 0.182 | 0.622 | 1.000 | 1.000 |
| 2_5_1 | 0.695 | 0.913 | 0.870 | 0.949 |
| 2_7_1 | 0.754 | 1.000 | 1.000 | 1.000 |
| 4_2_3 | 0.938 | 0.909 | 1.000 | 0.405 |
| 4_3_1 | 0.786 | 0.765 | 0.828 | 0.537 |
| 4_4_2 | 0.9736 | 0.020 | 1.000 | 1.000 |
| 4_6_1 | 1.000 | 1.000 | 0.038 | 0.689 |
| 4_8_1 | *0.084* | 0.169 | 1.000 | 0.935 |
| 5_1_2 | 0.847 | 1.000 | 1.000 | 0.399 |
| 6_1_4 | *0.097* | *0.066* | 0.016 | 0.837 |
| 6_2_1 | 0.933 | 0.741 | 0.863 | 0.857 |
| 6_2_2 | 0.711 | 0.679 | 0.844 | 0.784 |

[1]Significance of differences were determined by permutation testing. Significant differences (p < 0.05) are marked in bold, while differences in the range 0.05 < p < 0.1 are italicized.

Discussion

With the SNuPE based GA-map assay we have obtained a 16S rRNA gene microarray of high specificity and sensitivity with only a few probes. The obvious benefit of this is that the assay enables high-throughput applications.

The most surprising biological finding in our data was that *B. longum* were significantly overrepresented in the IgE sensitised group at 360 days, in addition to low p-values for 10 days and 120 days. This finding has also been independently confirmed by q-PCR for the IM-PACT data (unpublished results). Taken together, the multiple independent correlations support the validity of the observations. The surprise was because most previous work has actually suggested that *B. longum* is protective with respect to sensitisation. Experiments with mouse models, however, have shown that the time and order of bifidobacterial colonization are important for the immunomodulatory effects. This may explain the differences in effects between different studies.

We also found that the Firmicutes subgroup containing streptococci and enterococci were significantly overrepresented in for the IgE sensitized group. Relatively little is described about these bacterial groups with respect to sensitisation. It has, however, been suggested that *S. pneumonia* infections can be correlated to increased IgE levels in chronic bronchitis. Thus, there could be common underlying mechanisms for the infant and bronchitis sensitization.

In short, this study demonstrates the usefulness of the GA-map infant assay in determining variations in the composition of the gut microbiota. Such information could lead to early diagnosis of disease and better prophylactic or therapeutic treatments of various gut related diseases.

The invention claimed is:

1. A set of oligonucleotide probes, said set comprising:
   (a) an oligonucleotide probe consisting of a nucleotide sequence ACGCTTGCACCCT (SEQ ID NO 1), optionally with up to three substituted bases, optionally with 1 to 10 additional nucleotides added to the 5' and/or 3' end, or AGGGTGCAAGCGT (SEQ ID NO 27), optionally with up to three substituted bases, optionally with 1 to 10 additional nucleotides added to the 5' and/or 3' end;
   (b) an oligonucleotide probe consisting of a nucleotide sequence CGATCCGAAAACCTTCTTCACT (SEQ ID NO 2), optionally with up to three substituted bases, optionally with 1 to 10 additional nucleotides added to the 5' or 3' end, or AGTGAAGAAGGTTTTCGGATCG (SEQ ID NO 28), optionally with up to three substituted bases, optionally with 1 to 10 additional nucleotides added to the 5' or 3' end;
   (c) an oligonucleotide probe consisting of a nucleotide sequence GGACAACGCTTGCCAC (SEQ ID NO 3), optionally with up to three substituted bases, optionally with 1 to 10 additional nucleotides added to the 5' or 3' end, or GTGGCAAGCGTTGTCC (SEQ ID NO 29), optionally with up to three substituted bases, optionally with 1 to 10 additional nucleotides added to the 5' or 3' end;
   (d) an oligonucleotide probe consisting of a nucleotide sequence CGTAGGCGGTTCGTCGCGT (SEQ ID NO 4), optionally with up to three substituted bases, optionally with 1 to 10 additional nucleotides added to the 5' or 3' end, or ACGCGACGAACCGCCTACG (SEQ ID NO 30), optionally with up to three substituted bases, optionally with 1 to 10 additional nucleotides added to the 5' or 3' end; and
   (e) one or more oligonucleotide probes consisting of a nucleotide sequence selected from those recited in Table 1, optionally with up to three substituted bases, optionally with 1 to 10 additional nucleotides added to the 5' or 3' end; and optionally
   (f) one or more oligonucleotide probes consisting of a nucleotide sequence selected from those recited in Table 2 and Table 3, optionally with up to three substituted bases, optionally with 1 to 10 additional nucleotides added to the 5' or 3' end, wherein each of oligonucleotide probes (a) to (e), or if present (f), is labelled with a moiety for detection or manipulation or is immobilized onto one or more solid supports.

2. The oligonucleotide probe set of claim 1, wherein component (f) is present in the probe set and is one or more oligonucleotides consisting of a nucleotide sequence selected from those recited in Table 2.

3. The oligonucleotide probe set of claim 1, wherein said moiety is colorimetric, chemiluminescent, chromogenic, radioactive, fluorescent, an enzyme, an antibody fragment, a His-tag, biotin or streptavidin.

4. The oligonucleotide probe set of claim 1, wherein the one or more solid supports is selected from particles, sheets, gels, filters, membranes, fibres, capillaries, chips, microtitre strips, slides, tubes, plates and wells.

5. The oligonucleotide probe set of claim 4, wherein said solid support, is a magnetic particle.

6. The oligonucleotide probe set of claim 4, wherein said solid support is labelled with a dye or a plurality of dyes.

* * * * *